United States Patent
Ekwuribe et al.

(12)

(10) Patent No.: US 7,169,889 B1
(45) Date of Patent: *Jan. 30, 2007

(54) INSULIN PRODRUGS HYDROLYZABLE IN VIVO TO YIELD PEGLYLATED INSULIN

(75) Inventors: Nnochiri N. Ekwuribe, Cary, NC (US); Muthukumar Ramaswamy, Cary, NC (US); Jayanthi Rajagopalan, Cary, NC (US)

(73) Assignee: Biocon Limited, Bangalore (IN)

(*) Notice: Subject to any disclaimer, the term of this patent is extended or adjusted under 35 U.S.C. 154(b) by 0 days.

This patent is subject to a terminal disclaimer.

(21) Appl. No.: 10/018,879

(22) PCT Filed: Jun. 19, 2000

(86) PCT No.: PCT/US00/16879

§ 371 (c)(1),
(2), (4) Date: Aug. 5, 2002

(87) PCT Pub. No.: WO00/78302

PCT Pub. Date: Dec. 28, 2000

Related U.S. Application Data

(63) Continuation of application No. 09/336,548, filed on Jun. 19, 1999, now Pat. No. 6,309,633.

(51) Int. Cl.
*A61K 38/28* (2006.01)
*C07K 14/62* (2006.01)

(52) U.S. Cl. .......................................... 530/303; 514/3

(58) Field of Classification Search ................ 530/300, 530/322, 345, 409, 410, 411, 303; 514/2, 514/3, 8, 12, 21
See application file for complete search history.

(56) References Cited

U.S. PATENT DOCUMENTS

| 3,256,153 A | 6/1966 | Heimlich ...................... 167/82 |
| 3,868,356 A | 2/1975 | Smyth ...................... 260/112.7 |
| 3,919,411 A | 11/1975 | Glass et al. .............. 424/78.27 |
| 3,950,517 A | 4/1976 | Lindsay et al. ................. 514/3 |
| 4,003,792 A | 1/1977 | Mill et al. ..................... 195/63 |

(Continued)

FOREIGN PATENT DOCUMENTS

| DE | 196 32 440 A1 | 2/1998 |
| EP | 0 031 567 A2 | 7/1981 |
| EP | 0 092 918 B1 | 11/1983 |
| EP | 0 364 855 B1 | 2/1990 |
| EP | 0 381 070 A1 | 8/1990 |

(Continued)

OTHER PUBLICATIONS

Abuchowski, A. and F.F. Davis, "Soluble Polymer–Enzyme Adducts," pp. 368–383, Enzymes as Drugs, J. S. Holcenberg, John Wiley, 1981.
Akiyama, M. et al., "The Synthesis of New Derivatives of 1-.beta.–D–Arabinofuranosylcytosine," Chem. Pharm. Bull., 1978, 26(3): p. 981–984.
Allcock et al., "Contemporary Polymer Chemistry," 394–403 (2nd. ed., 1991).

(Continued)

*Primary Examiner*—Jeffrey E. Russel
(74) *Attorney, Agent, or Firm*—Marianne Fuierer; William A. Barrett; Moore & Van Allen PLLC

(57) ABSTRACT

The present invention relates generally to hydrolyzable drug-oligomer conjugates, pharmaceutical compositions comprising such conjugates, and to methods for making and using such conjugates and pharmaceutical compositions. For example, a conjugate of insulin, PEG, and oleic acid can be orally administered.

25 Claims, 3 Drawing Sheets

Synthesis Scheme for Drug–Oligomer Conjugates

U.S. PATENT DOCUMENTS

| | | | |
|---|---|---|---|
| 4,044,196 A | 8/1977 | Hüper et al. | 526/271 |
| 4,087,390 A | 5/1978 | Shields | 260/8 |
| 4,093,574 A | 6/1978 | Shields | 260/8 |
| 4,100,117 A | 7/1978 | Shields | 260/8 |
| 4,179,337 A | 12/1979 | Davis et al. | 435/181 |
| 4,223,163 A | 9/1980 | Guilloty | 568/618 |
| 4,229,438 A | 10/1980 | Fujino et al. | 424/177 |
| 4,253,998 A | 3/1981 | Sarantakis | 525/54.11 |
| 4,277,394 A | 7/1981 | Fujino et al. | 530/330 |
| 4,338,306 A | 7/1982 | Kitao et al. | 514/4 |
| 4,348,387 A | 9/1982 | Brownlee et al. | 514/4 |
| 4,410,547 A | 10/1983 | Ueno et al. | 424/317 |
| 4,469,681 A | 9/1984 | Brownlee et al. | 514/4 |
| 4,472,382 A | 9/1984 | Labrie et al. | 514/15 |
| 4,526,938 A | 7/1985 | Churchill et al. | |
| 4,554,101 A | 11/1985 | Hopp | 530/324 |
| 4,579,730 A | 4/1986 | Kidron et al. | 514/3 |
| 4,585,754 A | 4/1986 | Meisner et al. | 514/8 |
| 4,622,392 A | 11/1986 | Hong et al. | 536/29 |
| 4,684,524 A | 8/1987 | Eckenhoff et al. | 424/469 |
| 4,698,264 A | 10/1987 | Steinke | 428/402.2 |
| 4,717,566 A | 1/1988 | Eckenhoff et al. | 424/438 |
| 4,744,976 A | 5/1988 | Snipes et al. | 424/408 |
| 4,772,471 A | 9/1988 | Vanlerberghe et al. | 424/450 |
| 4,797,288 A | 1/1989 | Sharma et al. | 424/476 |
| 4,801,575 A | 1/1989 | Pardridge | 514/4 |
| 4,839,341 A | 6/1989 | Massey et al. | 514/4 |
| 4,840,799 A | 6/1989 | Appelgren et al. | 424/493 |
| 4,849,405 A | 7/1989 | Ecanow | 514/3 |
| 4,917,888 A | 4/1990 | Katre et al. | 514/12 |
| 4,935,246 A | 6/1990 | Ahrens | 424/490 |
| 4,946,828 A | 8/1990 | Markussen | 514/3 |
| 4,957,910 A | 9/1990 | Sutton et al. | 514/182 |
| 4,963,367 A | 10/1990 | Ecanow | 424/485 |
| 4,994,439 A | 2/1991 | Longenecker et al. | 514/3 |
| 5,013,556 A | 5/1991 | Woodle et al. | 424/450 |
| 5,055,300 A | 10/1991 | Gupta | 424/409 |
| 5,055,304 A | 10/1991 | Makino et al. | 424/465 |
| 5,089,261 A | 2/1992 | Nitecki et al. | 424/85.2 |
| 5,093,198 A | 3/1992 | Speaker et al. | 428/402.21 |
| 5,099,074 A | 3/1992 | Mueller et al. | 568/617 |
| 5,108,568 A | 4/1992 | Van Alstine | |
| 5,122,614 A | 6/1992 | Zalipsky | 548/520 |
| 5,157,021 A | 10/1992 | Balschmidt et al. | 514/3 |
| 5,162,430 A | 11/1992 | Rhee et al. | 525/54.1 |
| 5,164,366 A | 11/1992 | Balschmidt et al. | 514/3 |
| 5,202,415 A | 4/1993 | Jonassen et al. | 530/303 |
| 5,206,219 A | 4/1993 | Desai | 514/3 |
| 5,283,236 A | 2/1994 | Chiou | 514/2 |
| 5,286,637 A | 2/1994 | Veronese et al. | 435/183 |
| 5,292,802 A | 3/1994 | Rhee et al. | 525/54.1 |
| 5,298,410 A | 3/1994 | Phillips et al. | 435/188 |
| 5,304,473 A | 4/1994 | Belagaje et al. | 435/69.7 |
| 5,308,889 A | 5/1994 | Rhee et al. | 523/113 |
| 5,312,808 A | 5/1994 | Shorr et al. | 514/6 |
| 5,320,840 A | 6/1994 | Camble et al. | 424/85.1 |
| 5,324,775 A | 6/1994 | Rhee et al. | 525/54.2 |
| 5,328,955 A | 7/1994 | Rhee et al. | 525/54.1 |
| 5,359,030 A | 10/1994 | Ekwuribe | 530/303 |
| 5,405,621 A | 4/1995 | Sipos | 424/490 |
| 5,405,877 A | 4/1995 | Greenwald et al. | 514/772.3 |
| 5,413,791 A | 5/1995 | Rhee et al. | 424/422 |
| 5,415,872 A | 5/1995 | Sipos | 424/490 |
| 5,428,128 A | 6/1995 | Mensi-Fattohi et al. | 530/302 |
| 5,438,040 A | 8/1995 | Ekwuribe | 514/3 |
| 5,444,041 A | 8/1995 | Owen et al. | 514/2 |
| 5,446,091 A | 8/1995 | Rhee et al. | 525/54.1 |
| 5,457,066 A | 10/1995 | Frank et al. | 435/68.1 |
| 5,461,031 A | 10/1995 | De Felippis | 514/4 |
| 5,468,478 A | 11/1995 | Saifer et al. | 424/78.27 |
| 5,504,188 A | 4/1996 | Baker et al. | 530/304 |
| 5,506,203 A | 4/1996 | Backstrom et al. | 514/4 |
| 5,518,998 A | 5/1996 | Backstrom et al. | 514/3 |
| 5,523,348 A | 6/1996 | Rhee et al. | 525/54.1 |
| 5,529,915 A | 6/1996 | Phillips et al. | 435/188 |
| 5,545,618 A | 8/1996 | Buckley et al. | 514/12 |
| 5,550,188 A | 8/1996 | Rhee et al. | 525/54.1 |
| 5,567,422 A | 10/1996 | Greenwald | 424/78.3 |
| 5,606,038 A | 2/1997 | Regen | 536/6.5 |
| 5,612,460 A | 3/1997 | Zalipsky | 530/391.9 |
| 5,631,347 A | 5/1997 | Baker et al. | 530/303 |
| 5,637,749 A | 6/1997 | Greenwald | 558/6 |
| 5,643,575 A | 7/1997 | Martinez et al. | 424/194.1 |
| 5,646,242 A | 7/1997 | Baker et al. | 530/303 |
| 5,650,388 A | 7/1997 | Shorr et al. | 514/6 |
| 5,658,878 A | 8/1997 | Backstrom et al. | 514/3 |
| 5,681,567 A | 10/1997 | Martinez et al. | 424/178.1 |
| 5,681,811 A | 10/1997 | Ekwuribe | 514/8 |
| 5,693,609 A | 12/1997 | Baker et al. | 514/3 |
| 5,693,769 A | 12/1997 | Kahne et al. | 536/5 |
| 5,700,904 A | 12/1997 | Baker et al. | 530/305 |
| 5,707,648 A | 1/1998 | Yiv | 424/450 |
| 5,714,639 A | 2/1998 | Bowman et al. | 568/620 |
| 5,738,846 A | 4/1998 | Greenwald et al. | 424/85.7 |
| 5,747,445 A | 5/1998 | Backstrom et al. | 514/4 |
| 5,747,642 A | 5/1998 | De Felippis | 530/304 |
| 5,750,497 A | 5/1998 | Havelund et al. | 514/3 |
| 5,766,620 A | 6/1998 | Heiber et al. | 424/436 |
| 5,824,638 A | 10/1998 | Burnside et al. | 514/3 |
| 5,830,853 A | 11/1998 | Backstrom et al. | 514/4 |
| 5,830,918 A | 11/1998 | Sportsman et al. | 514/648 |
| 5,849,860 A | 12/1998 | Hakimi et al. | 528/370 |
| 5,853,748 A | 12/1998 | New | 424/439 |
| 5,854,208 A | 12/1998 | Jones et al. | 514/3 |
| 5,856,451 A | 1/1999 | Olsen et al. | 530/402 |
| 5,866,538 A | 2/1999 | Norup et al. | 514/3 |
| 5,874,111 A | 2/1999 | Maitra et al. | 424/499 |
| 5,898,028 A | 4/1999 | Jensen et al. | 514/4 |
| 5,902,588 A | 5/1999 | Greenwald et al. | 424/278.1 |
| 5,905,140 A | 5/1999 | Hansen | 530/303 |
| 5,907,030 A | 5/1999 | Shen et al. | 530/331 |
| 5,922,675 A | 7/1999 | Baker et al. | 514/4 |
| 5,932,462 A | 8/1999 | Harris et al. | 435/188 |
| 5,942,248 A | 8/1999 | Barnwell | 242/457 |
| 5,948,751 A | 9/1999 | Kimer et al. | 514/4 |
| 5,952,008 A | 9/1999 | Backstrom et al. | 424/499 |
| 5,952,297 A | 9/1999 | De Felippis et al. | 514/3 |
| 5,962,267 A | 10/1999 | Shin et al. | 435/69.4 |
| 5,968,549 A | 10/1999 | New et al. | 424/450 |
| 5,969,040 A | 10/1999 | Hallahan et al. | 525/54.1 |
| 5,981,709 A | 11/1999 | Greenwald et al. | 530/351 |
| 5,985,263 A | 11/1999 | Lee et al. | 424/85.2 |
| 6,004,574 A | 12/1999 | Backstrom et al. | 424/434 |
| 6,011,008 A | 1/2000 | Domb et al. | 514/8 |
| 6,025,325 A | 2/2000 | Campfield et al. | 514/2 |
| 6,034,054 A | 3/2000 | De Felippis et al. | 514/4 |
| 6,043,214 A | 3/2000 | Jensen et al. | 514/3 |
| 6,051,551 A | 4/2000 | Hughes et al. | 514/3 |
| 6,063,761 A | 5/2000 | Jones et al. | 514/3 |
| 6,093,391 A | 7/2000 | Kabanov et al. | 424/85.1 |
| 6,113,906 A | 9/2000 | Greenwald et al. | 414/194.1 |
| 6,165,976 A | 12/2000 | Backstrom et al. | 514/3 |
| 6,177,087 B1 | 1/2001 | Greenwald et al. | 424/278.1 |
| 6,191,105 B1 | 2/2001 | Ekwuribe et al. | 514/3 |
| 6,200,602 B1 | 3/2001 | Watts et al. | 424/463 |
| 6,211,144 B1 | 4/2001 | Havelund | 514/4 |
| 6,248,363 B1 | 6/2001 | Patel et al. | 424/497 |
| 6,251,856 B1 | 6/2001 | Markussen et al. | 514/3 |
| 6,258,377 B1 | 7/2001 | New et al. | 424/450 |
| 6,268,335 B1 | 7/2001 | Brader | 514/3 |
| 6,306,440 B1 | 10/2001 | Backstrom et al. | 424/499 |

| | | | |
|---|---|---|---|
| 6,309,633 B1 | 10/2001 | Ekwuribe et al. | 424/85.1 |
| 6,310,038 B1 | 10/2001 | Havelund | 514/4 |
| 6,323,311 B1 | 11/2001 | Liu et al. | 530/303 |
| 6,335,316 B1 | 1/2002 | Hughes et al. | 514/3 |

FOREIGN PATENT DOCUMENTS

| | | |
|---|---|---|
| EP | 0 483 465 | 8/1995 |
| EP | 0 621 777 | 9/1996 |
| EP | 0 597 007 | 10/1996 |
| EP | 0 822 218 A2 | 2/1998 |
| EP | 0 797 615 | 1/1999 |
| GB | 1 492 997 | 11/1977 |
| JP | 01207320 | 8/1989 |
| JP | 01254699 | 10/1989 |
| WO | WO 93/01802 | 2/1993 |
| WO | WO 95/09831 | 4/1995 |
| WO | WO 95/30641 | 11/1995 |
| WO | WO 97/14740 | 4/1997 |
| WO | WO 98/07745 | 2/1998 |
| WO | WO 99/32134 | 7/1999 |
| WO | WO 00/43034 A3 | 7/2000 |
| WO | WO 00/43034 | 7/2000 |
| WO | WO 00/78302 A1 | 12/2000 |
| WO | WO 01/12230 | 2/2001 |
| WO | WO 02/098232 A1 | 12/2002 |
| WO | WO 02/098446 A1 | 12/2002 |
| WO | WO 03/02208 A2 | 3/2003 |
| WO | WO 03/022208 A3 | 3/2003 |
| WO | WO 03/022210 A2 | 3/2003 |
| WO | WO 03/022996 A2 | 3/2003 |
| WO | WO 2003022996 A3 | 3/2003 |

OTHER PUBLICATIONS

Ansell, S. et al., "Application of Oligo–(14–amino–3,6,9, 12–tetraoxatetradecanoic acid) Lipid Conjugates as Steric Barrier Molecules in Liposomal Formulations," Bioconjugate Chem., 10: 653–666 (1999).

Banting et al., "Pancreatic Extracts in the Treatment of Diabetes Mellitus: Preliminary Report," Can. Med. Assoc. J., 145(10): 1281–1286 (1991).

Baudys et al., "Stabilization and Intestinal Absorption of Human Calcitonin," J. Contr. Rel. vol. 39, pp. 145–151 (1996).

Baudys, M. et al, "Synthesis and Characterization of Different Glycosylated Derivatives of Insulin" Proceed. Intern. Symp. Cont. Rel. Bioactive. Mater., 1992, 19: 210–211.

Brange, J., "Galenics of Insulin: The Physico–Chemical and Pharmaceutical Aspects of Insulin and Insulin Preparations," Novo Research Institute, Denmark, 18–100 (1987).

Chen et al., "Synthesis and Properties of AMA Amphiphiles," J. Org. Chem., 64: 6870–6873 (1999).

Chien, Y. W., Novel Drug Delivery Systems, pp. 678–679, Marcell Deffer, Inc., New York, N.Y., 1992.

Coombes, A.G.A. et al., "Biodegradable Polymeric Microparticles for Drug Delivery and Vaccine Formulation: the Surface Attachment of Hydrophilic Species Using the Concept of Poly(Ethylene Glycol) Anchoring Segments," Biomaterials, 18: 1153–1161 (1997).

Coudert et al., "A Novel, Unequivocal Synthesis of Polyethylene Glycols," Synthetic Communications, 16(1): 19–26 (1986).

Forst et al., "New Aspects on Biological Activity of C–peptide in IDDM Patients," Exp. Clin. Endocrinol. Diabetes, 196: 270–276 (1998).

Francis et al., "Polyethylene Glycol Modification: Relevance of Improved Methodology to Tumour Targeting," J. Drug Targeting, 3: 321–340 (1996).

Gombotz et al., "Biodegradable Polymers for Protein and Peptide Drug Delivery," Bioconjugate Chem., 6: 332–351 (1995).

A. Guzman & R. Garcia, "Effects of Fatty Ethers and Stearic Acid on the Gastrointestinal Absorption of Insulin," PRHSJ, 9(2), 155–159 (1990).

Harris, J. Milton, "Laboratory Synthesis of Polyethylene Glycol Derivatives," J. Macromol. Science—Rev. Macromol. Chem. Phys., C25(3): 325–373 (1985).

Hashimoto et al., "Synthesis of Palmitoyl Derivatives of Insulin and Their Biological Activities," Pharmaceutical Research, 6(2): 171–176 (1989).

Igarashi, R. et al, "Biologically Active Peptides Conjugated with Lecithin for DDS" Proceed. Intern. Symp. Cont. Rel. Bioactive. Mater. 1990, 17 367–368.

Kemmler et al., "On the Nature and Subcellular Localization of the Proinsulin Converting Enzymes," Federation Proceedings, 30(Abstract 924): 1210Abs (1971).

Kemmler et al., "Studies on the Conversion of Proinsulin to Insulin: I. Conversion in Vitro with Trypsin and Carboxypeptidase B," The Journal of Biological Chemistry, 246(22) 6786–6791 (Nov. 25, 1971).

D.G. Lindsay & S. Shall, "The Acetylation of Insulin," Biochem. J., 121: 737–745 (1971).

Mesiha et al., "Hypoglycaemic effect of oral insulin preparations containing Brij 35, 52, 58 or 92 and stearic acid," J. Pharm. Pharmacol., 33: 733–734 (1981).

Neubauer et al., "Influence of Polyethylene Glycol Insulin on Lipid Tissues of Experimental Animals," Diabetes, 32: 953–958 (Oct. 1983).

Nucci, et al. "The Therapeutic Value of Poly(ethylen Glycol)—Modified Proteins" Ac. Drug. Del. Rev. 6: 133–151 1991.

Patel et al. "Oral Administration of Insulin By Encapsulation Within Liposomes" FEBS Lett. 62(1) 60–63 1976.

Russell–Jones, G. J. "Vitamin B12 Drug Delivery", Proceed. Intern. Symp. Control. Rel. Bioactive. Mater., 1992, 19: 102–103.

Santiago, N. et al, "Oral Immunization of Rats with Influenza Virus M Protein (M1) Microspheres," Proceed. Intern. Symp. Cont. Rel. Bioactive. Mater., 1992, 19: 116–117.

Savva et al., "Effect of PEG Homopolymer and Grafted Amphiphilic PEG–Palmityl on the Thermotropic Phase Behavior of 1,2–Dipalmitoyl–SN–Glycero–3–Phosphocholine Bilayer," Journal of Liposome Research, 9(3): 357–365 (1999).

Shen et al., "(C) Means to Enhance Penetration, (3) Enhancement of polypeptide and protein absorption by macromolecular carriers via endocytosis and transcytosis," Advanced Drug Delivery Reviews, 8: 93–113 (1992).

G. Sirokman & G.D. Fasman, "Refolding and proton pumping activity of a polyethylene glycol–bacteriorhodopsin water–soluble conjugate," Protein Science, 2: 1161–1170 (1993).

Szleifer, I. et al., "Spontaneous Liposome Formation Induced by Grafted Poly(Ethylene Oxide) Layers: Theoretical Prediction and Experimental Verification," Proceedings of the National Academy of Sciences of the United States of America, 95(3): 1032–1037 (Feb. 3, 1998).

Taniguchi, T. et al, "Synthesis of Acyloyl Lysozyme and Improvement of its Lymphatic Transport Following Small Intestinal Administration in Rats" Proceed. Intern. Symp. Control. Rel. Bioactive. Mater., 1992, 19: 104–105.

V.P. Torchilin, "Immunoliposomes and PEGylated Immunoliposomes: Possible Use for Targeted Delivery of Imaging Agents," Immunomethods, 4: 244–258 (1994).

Tyle, Praveen, "Iontophoretic Devices for Drug Delivery," Pharma Research, 3:6 318–326 (1986).

Wahren et al., "Role of C–peptide in Human Physiology," Am. J. Physiol. Endocrinol. Metab., 278: E759–E768 (2000).

J. Wei & G.D. Fasman, "A Poly(ethylene glycol) Water–soluble Conjugate of Porin: Refolding to the Native State," Biochemistry, 34:6408–6415 (1995).

Zalipsky et al., "Peptide Attachment to Extremities of Liposomal Surface Grafted PEG Chains: Preparation of the Long–Circulating Form of Laminin Pentapeptide, YIGSR," Bioconjugate Chem. 6: 705–708 (1995).

Aoshima et al.; "$N^4$–Behenoyl–1–β–D–Arabinofuranosylcytosine as a Potential New Antitumor Agent" Cancer Research 37 2481–2486 (1977).

Baker et al.; "Prodrugs of 9–β–D–Arabinofuranosyladenine. 1. Synthesis and Evaluation of Some 5'– (O–Acyl) Derivatives" Journal of Medicinal Chemistry 21:12 1218–1221 (1978).

Banting et al.; "Pancreatic Extracts in the Treatment of Diabetes Mellitus" The Canadian Medical Association Journal 12 141–146 (1992).

Boccu et al.; "Pharmacokinetic Properties of Polyethylene Glycol Derivatized Superoxide Dismutase" Pharmacological Research Communications 14:2 113–120 (1982).

Brange et al.; "Chemical Stability of Insulin. 1. Hydrolytic Degradation During Storage of Pharmaceutical Preparations" Pharmaceutical Research 9:6 715–726 (1992).

Brange et al.; "Chemical Stability of Insulin. 2. Formation of Higher Molecular Weight Transformation Products During Storage of Pharmaceutical Preparations" Pharmaceutical Research 9:6 727–734 (1992).

Conradi et al.; "The Influence of Peptide Structure on Transport Across Caco–2 Cells" Pharmaceutical Research 8:12 1453–1459(1991).

Delgado et al.; "The Uses and Properties of PEG–Linked Proteins" Critical Reviews in Therapeutic Drug Carrier Systems 9:3,4 249–304 (1992).

Engel et al.; "Insulin: Intestinal Absorption as Water–in–Oil–in–Water Emulsions" NATURE 219 856–857 (1968).

Fasano, Alessio; "Innovative strategies for the oral delivery of drugs and peptides" TIBTECH 16 152–157 (1998).

Gish et al.; "Nucleic Acids. 11. Synthesis of 5'–Esters of 1–β–D–Arabinofuranosylcytosine Possesing Antileukemic and Immunosuppressive Activity" Journal of Medicinal Chemistry 14:12 1159–1162 (1971).

Hong et al.; "Nucleoside Conjugates. 7. Synthesis and Antitumor Activity of 1–β–D–Arabinofuranosylcytosine Conjugates of Ether Lipids" J. Med. Chem. 29 2038–2044 (1986).

Hostetler et al.; "Synthesis and Antiretroviral Activity of Phospholipid Analogs of Azidothymidine and Other Antiviral Nucleosides" The Journal of Biological Chemistry 265:11 6112–6117 (1990).

T. King & C. Weiner.; "Preparation of Protein Conjugates with Alkoxypolyethylene Glycols" Int. J. Peptide Protein Res. 16 147–155 (1980).

Maislos et al.; "The Source of the Circulating Aggregate of Insulin in Type I Diabetic Patients Is Therapeutic Insulin" J. Clin. Invest.77 717–723 (1986).

Oka et al.; "Enhanced Intestinal Absorption of a Hydrophobic Polymer–Conjugated Protein Drug, Smancs, in an Oily Formulation" Pharmaceutical Research 7:8 852 855 (1990).

JC Price: Polyethylene Glycol, 355–361 (not dated).

Ratner et al.; "Persistent Cutaneous Insulin Allergy Resulting From High–Molecular–Weight Insulin Aggregates" Diabetes 39 728–733 (1990).

Robbins et al.; "Antibodies to Covalent Aggregates of Insulin in Blood of Insulin–Using Diabetic Patients" Diabetes 36 838–841 (1987).

Saffran et al.; "A Module for the Study of the Oral Administration of Peptide Hormones" Can J. Biochem. 57 548–553 (1979).

Saffran et al.; "A New Approach to the Oral Administration of Insulin and Other Peptide Drugs" Science 233 1081–1084 (1986).

Shichiri et al.; "Enteral Absorption of Water–in–Oil–in–Water Insulin Emulsions in Rabbits" Diabetologia 10 317–321 (1974).

Zalipsky et al.; "Chapter 21—Use of Functionalized Poly(Ethylene Glycol)s for Modification of Polypeptides" 347–370 (1992).

Hashimoto et al., "Synthesis of Palmitoyl Derivatives of Insulin and Their Biological Activites," Pharmaceutical Research, 6:2 171–176 (1989).

Krishnan, B. Radha, et al., "Stability and Physical Characteristics of Orally Active Amphiphilic Human Insulin Analog, Methoxy (Polyethylene Glycol) Hexanoyl Human Recombinant Insulin (HIM2)," Proceed. Int'l. Symp. Control. Rel. Bioact. Mater., 27 pp. 1038–1039 (2000).

Xia, Jiding, et al., "Effects of polyoxyethylene chain length distribution on the interfacial properties of polyethylene glycol n–dodecyl ether," Yingyong Huaxue, 2:4, pp. 59–65 (1985) (Abstract Only).

Zalipsky Samuel; Synthesis of an End–Group Functionalized Polyethylene Glycol–Lipid Conjugate for Preparation of Polymer–Grafter liposomes; Bloconjugate Chemistry; 1993; pp. 296–299; vol. 4; American Chemical Society.

Bone et al. "Successful Treatment of an Insulin Dependent Rat Model of Human Type I Diabetes with Orally Acitve Insulin" Program and Abstracts, 4th International Workshop on Lessons from Animal Diabetes. Omiya, Japan Nov. 1994 (Abstract).

Bone et al. "Successful Treatment of Type 1 Diabetes with Orally–Active Insulin: Studies in The Insulin Dependent BB/S Rat" Program and Abstracts, 55th Annual Meeting of the American Diabetes Association, Atlanta Georgia, Jun. 1995 (Abstract).

Ekwuribe et al. "Oral Insulin Delivery: Hydrolyzable Amphiphillic Oligomer Conjugates Prolong Glucose Reduction" Proceed. Int'l. Symp. Control. Rel. Bioact. Mater. 26:147–148 (1999).

Ekwuribe, Nnochiri "Conjugation–Stabilized Polypeptide Compositions, Therapeutic Delivery and Diagnostic Formulations Comprising Same, and Method of Making and Using the Same" Biotechnology Advances 14(4):575–576 (1996) (Abstract).

Radhakrishnan et al. "Chemical Modification of Insulin with Amphiphillic Polymers Improves Intestinal Delivery" Proceed, Int'l Symp. Control Rel. Bioact. Mater. 25:124–125 (1998) (Abstract).

Radhakrishnan et al. "Oral Delivery of Insulin: Single Selective Modification at B29–LYS With Amphiphillic Oligomer" Program and Abstracts, 1999 National Meeting of the Ameri. Assoc. Pharm. Scient., New Orleans. LA (1999) (Abstract).

Radharkrishnan et al. "Structure–Activity Relationship of Insulin Modified with Amphiphillic Polymers" Program and Abstracts, 1998 National Meeting of the Amer. Assoc. Pharm. Scient., San Francisco, CA Pharm. Sci. (1):S–59 (1998) (Abstract).

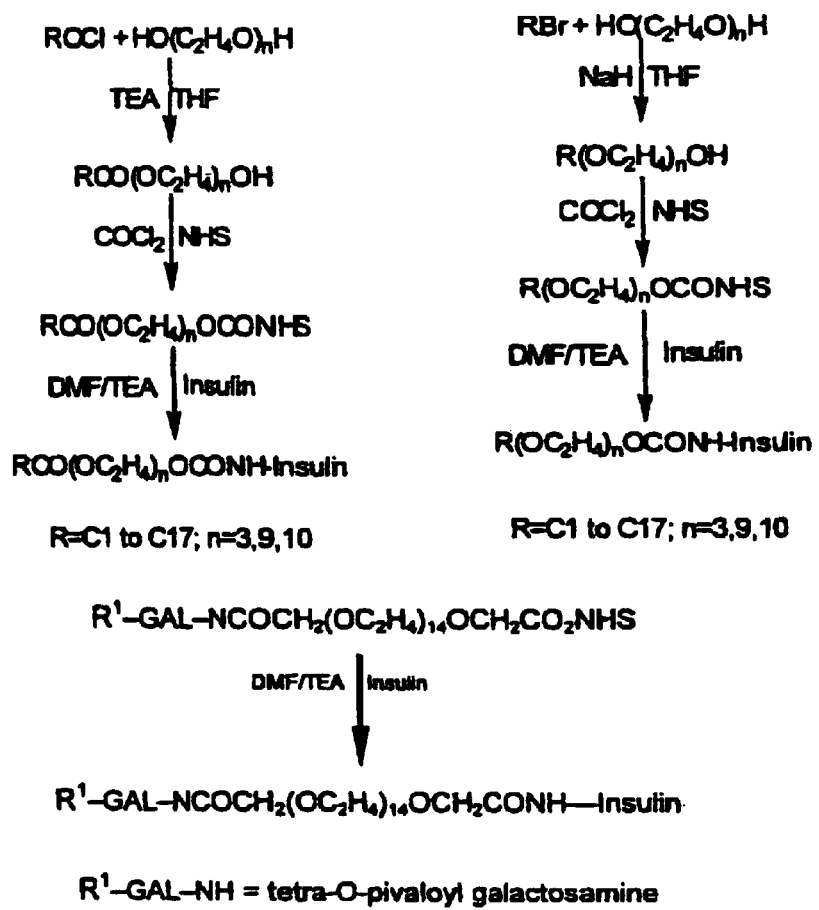
Figure 1. Synthesis Scheme for Drug–Oligomer Conjugates

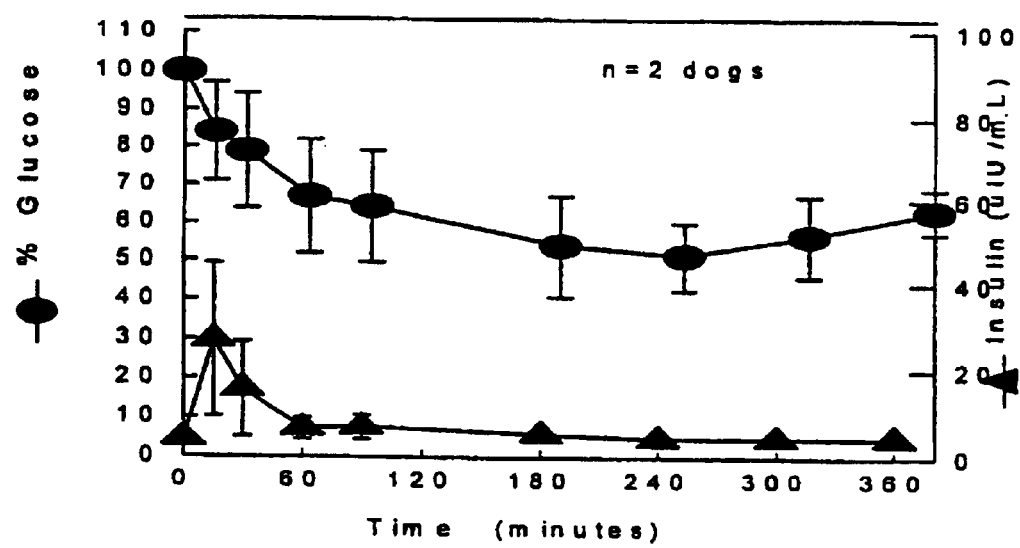
Figure 2. OLE-Ins Mix at 1mg/kg Oral Dose

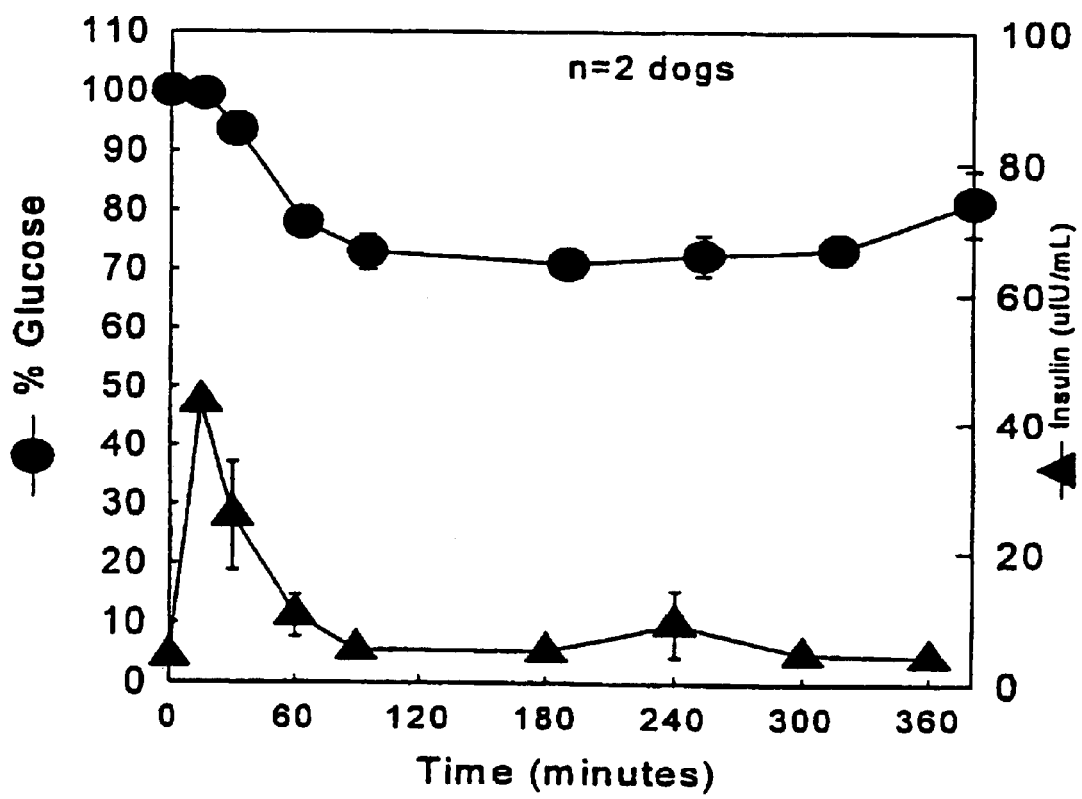
Figure 3. OCT-Ins Mix at 1 mg/kg Oral Dose

INSULIN PRODRUGS HYDROLYZABLE IN VIVO TO YIELD PEGLYLATED INSULIN

This application is a 35 U.S.C. §371 national phase application of international application serial no. PCT/US00/16879, filed Jun. 19, 2000 and published in English on Dec. 28, 2000, which is a continuation of U.S. application Ser. No. 09/336,548, filed Jun. 19, 1999, now U.S. Pat. No. 6,309,633, the contents of each of which are incorporated by reference herein in their entireties.

DESCRIPTION

1. Introduction

The present invention relates generally to hydrolyzable drug-oligomer conjugates, pharmaceutical compositions comprising such conjugates, and to methods for making and using such conjugates and pharmaceutical compositions.

2. Background of the Invention

Many peptides and proteins (collectively referred to herein as "polypeptides") are potentially useful as therapeutic agents but lack an adequate method of administration.

The usefulness of polypeptides as therapeutic agents is limited by the biological barriers that must be traversed before a polypeptide can reach its specific in vivo target. Parenterally administered polypeptides are readily metabolized by plasma proteases. Oral administration, which is perhaps the most attractive route of administration, is even more problematic. In the stomach, orally administered polypeptides risk enzymatic proteolysis and acidic degradation. Survival in the intestine is even more unlikely due to excessive proteolysis. In the lumen, polypeptides are continuously barraged by a variety of enzymes, including gastric and pancreatic enzymes, exo- and endopeptidases, and brush border peptidases. As a result, passage of polypeptides from the lumen into the bloodstream is severely limited.

There is therefore a need in the art for means which enable parenteral and oral administration of therapeutic polypeptides.

2.1 Routes of Administration of Polypeptide Drugs

The problems associated with oral and parenteral administration of polypeptides are well known in the pharmaceutical industry. Various strategies have been used in attempts to improve oral and parenteral delivery of polypeptides.

Penetration enhancers (e.g., salicylates, lipid-bile salt-mixed micelles, glycerides, and acylcamitines) has been investigated for improving oral administration. However, penetration enhancers frequently cause serious local toxicity problems, such as local irritation and toxicity, partial or complete abrasion of the epithelial layer, as well as tissue inflammation. Furthermore, penetration enhancers are usually co-administered with the polypeptide drug, and leakages from the dosage form are common.

Another common strategy for enhancing oral delivery is co-administration of the polypeptide drug with a protease inhibitor (e.g., aprotinin soybean trypsin inhibitor, and amastatin). Unfortunately, protease inhibitors also inhibit the desirable effects of proteases. Accordingly, methods and compositions are needed for effectively delivering polypeptide drugs in the absence of protease inhibitors.

Attempts have also been undertaken to modify the physiochemical properties of polypeptide drugs to enhance penetration of such drugs across mucosal membranes. One such approach has been to conjugate polypeptide drugs to lipophilic molecules; however, results have suggested that simply raising lipophilicity is not sufficient to increase paracellular transport.

Other methods for stabilizing polypeptides have been described. Thus, for example, Abuchowski and Davis have disclosed various methods for derivatizating enzymes to provide water-soluble, non-immunogenic, in vivo stabilized products ("Soluble polymers-Enzyme adducts", *Enzymes as Drugs*, Eds. Holcenberg and Roberts, J. Wiley and Sons, New York, N.Y., (1981)). Abuchowski and Davis disclose various ways of conjugating enzymes with polymeric materials, such as dextrans, polyvinyl pyrrolidones, glycopeptides, polyethylene glycol and polyamino acids. The resulting conjugated polypeptides are reported to retain their biological activities and solubility in water for parenteral applications. Furthermore, U.S. Pat. No. 4,179,337 discloses that polyethylene glycol renders proteins soluble and non-immunogenic. However, these polymeric materials do not contain components which improve intestinal mucosa binding or which facilitate or enhance membrane penetration. Thus, these conjugates are not intended for oral administration.

Meisner et al., U.S. Pat. No. 4,585,754, teaches that proteins may be stabilized by conjugating them with chondroitin sulfates. Products of this combination are usually polyanionic, very hydrophilic, and lack cell penetration capability; they are usually not intended for oral administration.

Mill et al., U.S. Pat. No. 4,003,792, teaches that certain acidic polysaccharides, such as pectin, algesic acid, hyaluronic acid and carrageenan, can be coupled to proteins to produce both soluble and insoluble products. Such polysaccharides lack the capacity to improve cell penetration characteristics and are not intended for oral administration.

Other researchers have shown that polyethylene glycol linked to a protein improves stability against denaturation and enzymatic digestion. (Boccu et al. Pharmacological Research Communication 14, 11–120 (1982)). However, these polymers do not contain components for enhancing membrane interaction. Thus, the resulting conjugates suffer from the same problems as noted above and are not suitable for oral administration.

Conjugation of polypeptides to low molecular weight compounds (e.g., aminolethicin, fatty acids, vitamin B12, and glycosides) has also been described (R. Igarishi et al., "Proceed. Intern. Symp. Control. Rel. Bioact. Materials, 17, 366, (1990); T. Taniguchi et al. Ibid 19, 104, (1992); G. J. Russel-Jones, Ibid, 19, 102, (1992); M. Baudys et al., Ibid, 19, 210, (1992)). The resulting polymers do not contain components necessary to impart both solubility and membrane affinity necessary for bioavailability following oral administration.

Encapsulation of proteinaceous drugs in an azopolymer film has also been employed as a means for enabling oral administration of polypeptide drugs (M. Saffan et al., in Science, 223, 1081, (1986)). The film is reported to survive digestion in the stomach but is degraded by microflora in the large intestine where the encapsulated protein is released. This approach is also known to lengthen the in vivo duration of action of polypeptide drug. However, the technique utilizes a physical mixture and does not facilitate the absorption of released protein across the membrane.

Similarly, liposomes have been used to stabilize polypeptide drug for oral as well as parenteral administration. A review of the use of liposomes is found in Y. W. Chien, "New Drug Delivery Systems", Marcel Dekker, New York, N.Y., 1992. Liposome-protein complexes are physical mixtures. Results of liposome-based administration are often erratic and unpredictable. Furthermore, use of liposomes can result in undesirable accumulation of the polypeptide drug in certain organs. Other disadvantages of liposome-based formulations include high cost, complex manufacturing processes requiring complex lyophilization cycles, and solvent incompatibilities.

Another approach for facilitating the oral delivery of polypeptide drugs is the use of "proteinoids" (Santiago, N. et al. "Oral Immunization of Rats with Influenza Virus M Protein (Ml) Microspheres", Abstract #A 221, Proc. Int. Symp. Control. Rel. Bioac. Mater., 19, 116 (1992)). Protenoids encapsulate the drug of interest in a polymeric sheath composed of highly branched amino acids. As with liposomes, the polypeptide drugs are not chemically bound to the proteinoid sphere; leakage of drug components from the dosage form is possible.

Attempts have been made to use emulsions as matrices for drug delivery of labile drugs (e.g., drugs such as insulin, which are susceptible to enzymatic, chemical, or physical degradation). However, in spite of preliminary reports on the efficacy of emulsion formulations in promoting the intestinal absorption of insulin in rats and rabbits (see Engel, S. et al., "Insulin: intestinal absorbtion as water-in-will-in-water emulsions," Nature, 219:856–857 (1968); Shichiri, Y. et al., "Enteral absorption of water-in-oil-in-water insulin emulsions and rabbits," Diabetologia, 10: 317–321 (1974)), subsequent research was abandoned because of the lability of the insulin and the need for excessive doses to maintain glucose homeostasis (Shichiri, Y. et al., "Increased intestinal absorbtion of insulin: an insulin suppository," J. Pharm. Pharamcol., 30:806–808 (1978); Block, L. et al. "Pharmaceutical Emulsions and Microemulsions," Pharmaceutical Dosage Forms: Disperse Systems, Vol. 2, p. 71 (1996)). Therefore, there remains a needed the art for methods and compositions which enable the use of emulsions and microemulsions for delivering labile drugs, such as insulin.

There is clearly a need in the art for means which (1) enable polypeptide drugs to survive in the gut and penetrate the gut epithelium to enter the bloodstream; (2) enable polypeptide drugs to survive in the bloodstream in an active form, and (3) provide polypeptide drugs having a delayed onset of action, and/or increased duration of action. The present invention provides means for solving each of these three important problems.

2.2 Diabetes and Insulin

Diabetes, a disorder of carbohydrate metabolism, has been known since antiquity. Diabetes results from insufficient production of or reduced sensitivity to insulin. Insulin is synthesized in the beta cells of the islets of Langerhans of the pancreas and is necessary for normal utilization of glucose by most cells in the body. In persons with diabetes, the normal ability to use glucose is inhibited, thereby increasing blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness.

There are two varieties of the diabetes. Type I is insulin-dependent diabetes mellitus, or IDDM. IDDM was formerly referred to as juvenile onset diabetes. In IDDM, insulin is not secreted by the pancreas and must be provided from an external source. Type II adult-onset diabetes can ordinarily be controlled by diet although in some advanced cases insulin is required.

Before the isolation of insulin in the 1920s, most patients died within a short time after onset. Untreated diabetes leads to ketosis, the accumulation of ketones, products of fat breakdown, in the blood; this is followed by acidosis (accumulation of acid in the blood) with nausea and vomiting. As the toxic products of disordered carbohydrate and fat metabolism continue to build up, the patient goes into diabetic coma.

Treatment of diabetes typically requires regular injections of insulin. The use of insulin as a treatment for diabetes dates to 1922, when Banting et al. ("Pancreatic Extracts in the Treatment of Diabetes Mellitus," Can. Med. Assoc. J., 12, 141–146 (1922)) showed that the active extract from the pancreas had therapeutic effects in diabetic dogs. Treatment of a diabetic patient in that same year with pancreatic extracts resulted in a dramatic, life-saving clinical improvement. Due to the inconvenience of insulin injections, insulin has been the focus of massive efforts to improve its administration and bioassimilation.

The insulin molecule consists of two chains of amino acids linked by disulfide bonds (mw 6,000). The β-cells of the pancreatic islets secrete a single chain precursor of insulin, known as proinsulin. Proteolysis of proinsulin results in removal of four basic amino acids (numbers 31, 32, 64 and 65 in the proinsulin chain: Arg, Arg, Lys, Arg respectively) and the connecting ("C") polypeptide. In the resulting two-chain insulin molecule, the A chain has glycine at the amino terminus, and the B chain has phenylalanine at the amino terminus.

Insulin may exist as a monomer, dimer or a hexamer formed from three of the dimers. The hexamer is coordinated with two $Zn^{++}$ atoms. Biological activity resides in the monomer. Although until recently bovine and porcine insulin were used almost exclusively to treat diabetes in humans, numerous variations in insulin between species are known. Porcine insulin is most similar to human insulin, from which it differs only in having an alanine rather than threonine residue at the B-chain C-terminus. Despite these differences most mammalian insulin has comparable specific activity. Until recently animal extracts provided all insulin used for treatment of the disease. The advent of recombinant technology allows commercial scale manufacture of human insulin (e.g., Humulin™ insulin, commercially available from Eli Lilly and Company, Indianapolis, Ind.).

The problems associated with oral administration of insulin to achieve euglycemia in diabetic patients are well documented in pharmaceutical and medical literature. Insulin is rapidly degraded by digestive enzymes in the GI tract which results in biologically inactive drug. The membrane permeability is also low due to the lack of sufficient lipophilicity(1). Oral delivery systems that effectively address these two big problems should improve intestinal absorption.

In our prior patents (U.S. Pat. Nos. 5,359,030; 5,438,040; and 5,681,811), we have shown that the amphiphilic modification of insulin improves its lipophilicity and stabilizes it against enzymatic degradation. However, the present inventors have surprisingly discovered insulin conjugates that enable oral delivery, provide delayed onset and/or extended duration of action, as well as dramatically enhancing the activity of insulin.

3. SUMMARY OF THE INVENTION

The present inventors have surprisingly discovered a new series of oligomers comprising a hydrophilic component and a lipophilic component linked by a hydrolyzable bond (e.g., an ester bond). When conjugated to a drug (as defined herein) and suitably formulated, these oligomers can facilitate oral delivery and delayed onset and/or extended duration of activity in the bloodstream. For ease of reference, the conjugates will be described herein as drug-oligomer conjugates; however, as will be apparent to those of skill in the art, the drug component may be conjugated to more than one hydrophile-lipophile component, and/or conjugated to individual hydrophile and lipophile components.

The oligomers of the present invention comprise a hydrophilic component and a lipophilic component. Suitable lipophilic components include, for example, straight or branched fatty acids or alkyl chains. Preferred lipophiles are natural fatty aids or alkyl chains. The fatty-acid component can be a straight or branched molecule having (saturated or unsaturated) carbon atoms and suitably range from two (2) to twenty-eight (28) carbon atoms. Most preferably, the fatty acid has from twelve (12) to twenty-two (22) carbon atoms.

The hydrophilic component is preferably a straight or branched poyethylene glycol (PEG) polymer, preferably having 2–130 PEG units, and more preferably 1–100 PEG units. In a specific embodiment, the drug component is insulin and the hydrophile is a PEG chain having 2–7, preferably 2–6, more preferably 3, 4 or 5 PEG units.

The hydrophilic and lipophilic components are preferably joined together by a hydrolyzable bond, such as an ester or carbonate bond. The use of a hydrolyzable bond ensures that when the conjugate has crossed the gut epithelium into the hydrophilic environment of the blood stream, the lipophilic component will be excised by hydrolysis of the hydrolyzable bond, thereby releasing the drug-hydrophile component of the conjugate. This is particularly important where the drug component is insulin and the hydrophilic component is a PEG chain which increases the activity of insulin.

In a preferred mode, where the conjugate is to be administered orally, the length and composition of the lipophilic components and the hydrophilic components may be adjusted to ensure that (1) the conjugate has sufficient amphiphilicity to traverse the gut epithelium, and (2) the activity of the therapeutic moiety is not eliminated once the lipophile has been severed by hydrolysis of the hydrolysable bond connecting the hydrophile and lipophile. Moreover, the amphiphilicity of the drug-oligomer conjugate may be adjusted as necessary to enable formulation of the drug in a lipophilic or hydrophilic carrier, or in an emulsion of microemulsion.

In a preferred aspect, the polypeptide-oligomer conjugates of the present invention have the following general formula:

 (Formula 1)

where
D is a therapeutic drug moiety;
H is a hydrophilic moiety selected from the group consisting of straight or branched PEG polymers having from 2 to 130 PEG subunits, and sugars;
L and L' are each a lipophilic moiety, independently selected from the group consisting of alkyl groups having 2–24 carbon atoms, cholesterol, and fatty acids;
o is a number from 1 to the maximum number of covalent bonding sites on H; and
p has a value of at least 1 and m+n+p together have a value of at least one and not exceeding the total number of covalent bonding sites on D for such substituents; the H—L bond(s) are hydrolyzable and the D—L' bond(s), when present are hydrolyzable.

In a narrower aspect, the drug-oligomer conjugates of the present invention have the formula:

 (Formula 2)

where
D is a therapeutic drug moiety;
H is a hydrophilic moiety selected from the group consisting of straight or branched PEG polymers having from 2 to 130 PEG subunits, and sugars;
L is a lipophilic moiety selected from the group consisting of alkyl groups having 2–24 carbon atoms, cholesterol, and fatty acids; and
o is a number from 1 to the maximum number of covalent bonding sites on H;
p is a number from 1 to the maximum number of covalent bonding sites on D;
the H—L bond is hydrolyzable.

In one aspect, the oligomers of the present invention comprise a subunit selected from the group consisting of:

 (Formula 3);

wherein n=3 to 25 and m=1 to 7;

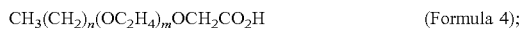 (Formula 4);

wherein n=3 to 25 and m=1 to 6;

 (Formula 5);

wherein n=3 to 25, m=1 to 7 and X=O;

 (Formula 6)

wherein m=0 to 5 and R=cholesterol or adamantane; or

 (Formula 7);

wherein m=0 to 14;

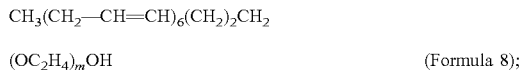 (Formula 8);

wherein m=0 to 7;

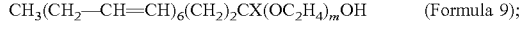 (Formula 9);

wherein m=1 to 7 and X=N or O.

Other unsaturated fatty acid components which can be used according to the present invention include oleic, linoleic, and linolenic acids.

The present inventors have also found that pegylation of insulin by $PEG_{2-7}$, preferably $PEG_3$ dramatically increases the activity of insulin. The present invention takes advantage of this surprising discovery by providing an insulin-$PEG_{2-7}$-lipophile conjugate in which the PEG-lipophile bond is hydrolyzable. In the bloodstream, the hydrolyzable PEG-lipophile bond is hydrolyzed, leaving the highly active insulin-PEG compound circulating in the blood.

In other embodiments, the conjugates of the present invention have the formula:

 (Formula 10)

wherein D, H, L and p are as described above and H' is as described for H above; and wherein the H—H' bond is hydrolyzable and the H'—L bond is not hydrolyzable; q is a number from 1 to the maximum number of covalent bonding sites on H at which an H' can be attached to H; and o is a number from 1 to the maximum number of covalent bonding sites at which an L substituent can be attached to H'. This arrangement permits the H and H' moieties to be selected so as to balance the hydrophilicity of the conjugate against the lipophilicity of the conjugate and (accounting for the hydrophilicity or lipophilicity of D) enabling the production of an amphiphilic conjugate, while at the same time, enabling the use of a small H moiety (e.g., H can be a short PEG chain having 2 to 10 PEG units) which enables or retains activity of the hydrolyzed D—H moiety. In other words, the hydrolyzable bond can be positioned at any point along the hydrophilic moiety which provides a hydrolyzed D—H moiety with maximum activity. Where D is insulin, H is preferably $PEG_{2-7}$; more preferably $PEG_2$, $PEG_3$, $PEG_4$ or $PEG_5$; most preferably $PEG_3$; and H' and L are selected to balance the lipophilicity and hydrophilicity of the conjugate to provide an amphiphilic conjugate, having the capacity to pass from the lumen of the intestine into the bloodstream.

In other embodiments, the conjugates of the present invention have the formulae:

  (Formula 11)

  (Formula 12); and

  (Formula 13)

wherein D, H, H' and L are as defined above; S is a spacer group selected from the group consisting of sugars, carbohydrates and glycerol; q is a number from 1 to the maximum number of covalent bonding sites on H; n is a number from 0 to the maximum number of covalent bonding sites on H'; o is a number from 1 to the maximum number of covalent bonding sites on S, when S is present or on H' when S is not present; and p is a number from 1 to the maximum number of covalent bonding sites on D; when S is not present, L is attached to H or H' (as in Formulas 1 and 2, respectively). Each of the Formulas, 11, 12 and 13 has at least 1 hydrolyzable bond. In Formula 11, the hydrolyzable bond can be S—L or S—H; in Formula 12, the hydrolyzable bond can be S—H or S—H'; in Formula 13, the hydrolyzable bond is H—H'.

The present invention also provides pharmaceutical formulations comprising the drug-oligomer conjugates. In a preferred aspect, the pharmaceutical formulations are emulsions or microemulsions. The drug-oligomer conjugates of the present invention have the important advantage that they are more readily incorporated into emulsion and microemulsion formulations. Furthermore, the lipophilicity/hydrophilicity of the conjugates can be readily adjusted by varying the molecular weight and structure of the hydrophilic and lipophilic components of the oligomer, in order to facilitate solubility in a specific emulsion or microemulsion formulation.

The present invention also provides methods for making and using the polypeptide-oligomer conjugates and pharmaceutical formulations comprising these conjugates.

3.1 Definitions

The terms "peptide," "polypeptide," and "protein" are used interchangeably herein and are intended to refer to amino acid sequences of any length.

As used herein the term "PEG" refers to straight or branched polyethylene glycol polymers and monomers. The term "PEG subunit" refers to a single polyethylene glycol unit, i.e.:

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity, e.g., fatty acid, cholesterol. Lipophiles are represented in the formulae herein as "L."

As used herein, the term "hydrophilic" means the ability to dissolve in water, and the term "hydrophilic moiety" or "hydrophile" refers to a moiety which is hydrophilic and/or which when attached to another chemical entity, increases the hydrophilicity of such chemical entity, e.g., sugars, PEG. Hydrophiles are represented in the formulae herein as "H" or "H'."

As used herein, the term "amphiphilic" means the ability to dissolve in both water and lipids, and the terms "amphiphilic moiety" and "amphipile" mean a moiety which is amphiphilic and/or which, when attached to a polypeptide or non-polypeptide drug, increases the amphiphilicity of the resulting conjugate, e.g., PEG-fatty acid oligomer, sugar-fatty acid oligomer.

As used herein, the term "covalently coupled," "linked," "bonded," "joined," and the like, with reference to the drug, hydrophile, and lipophile components of the drug-oligomer conjugates of the present invention, mean that the specified components are either directly covalently bonded to one another or indirectly covalently bonded to one another through an intervening moiety or components, such as a bridge, spacer, linker or the like, e.g. a sugar moiety or a glycerin moiety can act as a spacer between a PEG polymer and a fatty acid moiety (i.e., PEG-sugar-fatty acid or PEG-glycerine-fatty acid).

As used herein terms such as "non-hydrolyzable" and phrases such as "not hydrolyzable" are used to refer to bonds which cannot be hydrolyzed under any conditions, as well as carbamate, amide and other bonds which are not quickly hydrolyzed under normal physiological conditions.

As used herein, the term "drug" means a substance used to diagnose, characterize, cure, mitigate treat, prevent or allay the onset of a disease, disease state, or other physiological conditioner to enhance normal physiological functioning in humans and/or in non-human animals. The term includes pro-drugs, salts, esters, and other various forms of administerable drug substances. Drugs are represented in the formulae herein as "D."

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The tern "functional equivalent" is used herein to refer to a polypeptide which is an active analogue, derivative, fragment, truncation isoform or the like of a native polypeptide. A polypeptide is active when it retains some or all of the biological activity of the corresponding native polypeptide.

The term "immunizingly effective" is used herein to refer to an immune response which confers immunological cellular memory upon the subject of such immune response, with the effect that a secondary response (to the same or a similar immunogen) is characterized by one or more of the following: shorter lag phase in comparison to the lag phase resulting from a corresponding exposure in the absence of immunization; production of antibody which continues for a longer period than production of antibody for a corresponding exposure in the absence of such immunization; a change in the type and quality of antibody produced in comparison to the type and quality of antibody produced from such an exposure in the absence of immunization; a shift in class response, with IgG antibodies appearing in higher concentrations and with greater persistence than IgM; an increased average affinity (binding constant) of the antibodies for the antigen in comparison with the average affinity of antibodies for the antigen from such an exposure in the absence of immunization; and/or other characteristics known in the art to characterize a secondary immune response.

As used herein, "pharmaceutically acceptable" component (such as a salt, carrier, excipient or diluent) of a formulation according to the present invention is a component which (1) is compatible with the other ingredients of the formulation in that it can be combined with the drug-oligomer conjugates of the present invention without eliminating the biological activity of the drug-oligomer conjugates; and (2) is suitable for use with animals (including humans) without undue adverse side effects (such as toxicity, irritation, and allergic response). Side effects are "undue" when their risk outweighs the benefit provided by the pharmaceutical composition. Examples of pharmaceutically acceptable components include, without limitation, any of the standard pharmaceutical carriers such as phosphate buffered saline solutions, water, emulsions such as oil/water emulsion, microemulsions and various types of wetting agents.

As used herein, the term "native" used in reference to a polypeptide, such as insulin, is used to indicate that the polypeptide indicated has the amino acid sequence of the corresponding polypeptide as found in nature.

The terms "antigen" and "antigenic" as used herein are meant to describe a substance that induces an immune response when presented to immune cells of an organism. An antigen may comprise a single immunogenic epitope, or a multiplicity of immunogenic epitopes recognized by a B-cell receptor (i.e., antibody on the membrane of the B cell) or a T-cell receptor. Thus, as used herein, these terms refer to any substance capable of eliciting an immune response, e.g., Human Immunodeficiency Virus (HIV) antigens, Hepatitis virus antigens (HCV, HBV, HAV), and antigens from *Toxoplasmosis gondii*, Cytomegalovirus, *Helicobacter pylori*, Rubella, and the like, as well as haptens which may be rendered antigenic under suitable conditions known to those of skill in the art.

3.2 BRIEF DESCRIPTION OF THE DRAWINGS

FIG. 1 illustrates a synthesis scheme for making drug-oligomer conjugates.

FIG. 2 shows glucose response in dogs orally administered an OLE-insulin mixture at 1 mg/kg.

FIG. 3 shows glucose response in dogs orally administered an OCT-insulin mixture at 1 mg/kg.

4. DETAILED DESCRIPTION OF THE INVENTION

The present invention broadly relates to therapeutic and/or diagnostic drug-oligomer conjugates wherein a drug molecule is covalently bonded to a oligomer to form an amphiphilic conjugate. The oligomers comprise at least one hydrophilic moiety and least one lipophilic moiety. The moieties are variously linked by hydrolyzable bonds, such that upon hydrolysis of the hydrolyzable bond, an active drug-hydrophile (D—H) conjugate remains. The oligomers can advantegeously facilitate oral delivery while extending onset of activity of the polypeptide-oligomer conjugate in the blood stream.

4.1 Drug-oligomer Conjugates

The drug-oligomer conjugates are generally arranged as D—H—L or D—H—H'—L, wherein the H—L and H—H' bonds can be hydrolyzed in the blood stream to leave the D—H conjugate circulating in the blood stream. It will be appreciated that the various oligomers described herein (e.g., —H—L; —H—H'—L; —H—S—L; —H—S—H'—L; and —H—H'—S—L) are not to viewed as exclusive; any particular D may have one or more of these oligomers attached thereto, so long as appropriate covalent bonding sites are present. Thus, for example, native insulin has 3 covalent bonding sites, which may be occupied by one, two or three identical oligomers or any combination of the oligomers described herein. Additionally, the covalent bonding sites may be occupied by any of the hydrophile and lipophile components described herein.

The conjugates of the present invention have the following general formula:

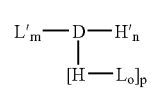

(Formula 1)

where

D is a therapeutic drug moiety;

H and H' are hydrophilic moieties, independently selected from the group consisting of straight or branched PEG polymers having from 2 to 130 PEG subunits, and sugars;

L and L' are lipophilic moieties, independently selected from the group consisting of alkyl groups having 2–24 carbon atoms, cholesterol, and fatty acids; and p has a value of at least 1 and m+n+p together have a value of at least one and not exceeding the total number of covalent bonding sites on D for such substituents;

wherein the H—L bond(s) are hydrolyzable and the D—L' bond(s), when present are hydrolyzable.

The numbers m+n+p cannot exceed the number of positions on D at which such moieties can be attached. For example, native human insulin has 3 covalent bonding sites; therefore m+n+p cannot exceed 3 where D is native human insulin. However, it will be appreciated that insulin, and other drugs, can be chemically modified to provide additional covalent bonding sites. Preferably, m+n+p will be in the range of from 1–10; more preferably 1–8; still more preferably 1–5, and most preferably 1,2,3, or 4. Where H of the H—L group is a PEG polymer (straight or branched), o is preferably from 1 to 3, more preferably 1 or 2, most preferably 2.

In a preferred mode, m+n=0, and p is at least 1. In an alternative aspect, p=0 and m and n are each at least 1. In this alternative aspect, the H—D bond is non-hydrolyzable and the L—D bond is hydrolyzable.

In a narrower aspect, the present invention provides drug-oligomer conjugates having the formula:

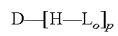

(Formula 2)

where

D is a therapeutic drug moiety;

H is a hydrophilic moiety selected from the group consisting of straight or branched PEG polymers having from 2 to 130 PEG subunits, and sugars;

L is a lipophilic moiety selected from the group consisting of alkyl groups having 2–24 carbon atoms, cholesterol, and fatty acids; and o is a number from 1 to the maximum number of covalent bonding sites on H;

p is a number from 1 to the maximum number of covalent bonding sites on D;

wherein the H $L_O$ bond is hydrolyzable.

In Formula 2, o is preferably 1–3, more preferably 1 or 2, and p is preferably 1–5, more preferably 1, 2 or 3.

The hydrolyzable bond is preferably selected from the group consisting of ester, and carbonate.

The present inventors have also found that pegylation of insulin by $PEG_{2-7}$ (preferably $PEG_3$) dramatically increases the activity of insulin. The present invention takes advantage of this surprising discovery by providing an insulin-PEG-lipophile conjugate in which the PEG-lipophile bond is hydrolyzable. In the bloodstream, the hydrolyzable PEG-lipophile bond will be hydrolyzed, leaving the highly active insulin-PEG compound circulating in the blood.

The lipophile of the insulin-PEG-lipophile conjugate is preferably selected so as to render the insulin inactive prior to hydrolysis of the PEG-lipophile hydrolyzable bond. As a result, the active form (insulin-PEG) is slowly released in the blood as the PEG-lipophile bond is hydrolyzed, thereby providing a gradual release of active insulin-PEG and a prolonged duration of action. The insulin-PEG-lipophile conjugates of the present invention may further be formulated with sufficient amphilicity to permit the conjugates to traverse the gut epithelium, thereby enabling oral administration of the conjugates. Amphiphilicity may be adjusted by means known in the art for shortening, lengthening and/or otherwise changing the conformation and/or structure of the PEG and/or the lipophile.

The present invention also provides methods for making and using the polypeptide-oligomer conjugates.

4.1.1 Drug Component of the Drug-oligomer Conjugates

The drug-oligomer conjugates of the present invention comprise a drug component. The drug component may be a small-molecule therapeutic drug moiety or a biologically active polypeptide. Suitable drugs are those which (1) are conjugatable to the oligomer of the present invention; and (2) retain some or all of their activity following hydrolytic removal of the lipophile component of the drug-oligomer conjugates (i.e., in the drug-hydrophile form).

In circumstances in which it is preferable for the drug component to remain attached to the hydrophile while circulating in the bloodstream (e.g., where lipophilic drugs benefit from the increased hydrophilicity contributed by the hydrophile, and/or where the hydrophile increases the activity of the drug), the hydrophile should be attached to the drug component of the oligomer by a non-hydrolyzable bond. Preferred non-hydrolyzable bonds include carbamate, amide, and secondary amine. However, it will be appreciated by those of skill in the art that it may be desirable in certain circumstances to attach one or more hydrophiles to the drug by a hydrolyzable bond. Thus, for example, it may be advantageous to retain less than all of the hydrophilic components during circulation to optimize hydrophilicity to improve circulation or to optimize activity of the circulating drug. Furthermore, attaching multiple hydrolyzable hydrophiles to the drug may be employed to improve circulation and delay onset of action of the drug. Thus, for example, administration of a mixture of drug-oligomer conjugates could ensure that some conjugates have almost immediate activity (i.e., only a few bonds to hydrolyze) while others become active on a time-delayed basis as multiple hydrolyzable bonds (joining the lipophile to the hydrophile and/or the hydrophile to the drug) are hydrolyzed.

The drug may be joined (1) directly to the hydrophile component of the oligomer by covalent bonding, or (2) indirectly through appropriate spacer groups (e.g., sugar groups as described below). The conjugated complex is preferably structurally arranged such that the hydrophilic moiety is attached directly to the drug and the lipophilic moiety is attached to the hydrophilic moiety. Furthermore, the drug may be attached to one or more additional lipophilic moieties and/or hydrophilic moieties, in the absence of or in combination with the oligomers.

While the examples set forth herein are illustratively directed to the use of insulin as the drug component of the drug-oligomer conjugates, it will be appreciated by those of skill in the art that the utility of the invention is not thus limited. A wide variety of drug species may be employed in the broad practice of the present invention. Suitable drug components are those which can be conjugated to the hydrophilic component of the oligomers described herein. Preferred drug components are active when the lipophile component of the drug-oligomer conjugates is excised by hydrolysis of the hydrolyzable bond, leaving the drug-hydrophile component intact. However, in an alternative embodiment, the hydrophile may joined to the drug component by a hydrolyzable bond, such that upon hydrolysis, the free, unconjugated, active drug is released.

In one aspect, the drug component of the drug-oligomer conjugates is a polypeptide. Suitable polypeptides are those which are biologically active, for example: adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives (see U.S. Pat. No. 4,229,438); bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides (see European Patent Publication Nos. 436189; 457195 and 496452 and Japanese Patent Unexamined Publication Nos. 94692/1991 and 130299/1991); endotherins; enkephalins; enkephalin derivatives (see U.S. Pat. No. 4,277,394 and European Patent Publication No. 31567); epidermal growth factor (EGF); erythropoietin (EPO); follicle-stimulating hormone (FSH); gailanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and α and β subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor: somatomedins; somatostatins derivatives (Sandostatin; see U.S. Pat. Nos. 4,087,390; 4,093,574; 4,100,117 and 4,253,998); substance P; superoxide dismutase; taftsin; tetragastrin; thrombopoietin (TPO); thymic humoral factor (THF); thymopoietin; thymosin; thymostmulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide;. vasopressins, and functional equivalents of such polypeptides.

In another aspect, the polypeptide is an antigen. May suitable antigens are known in the art, for example, antigens which can elicit an enhanced immune response, enhance an immune response and/or cause an immunizingly effective response to the following diseases and disease-causing agents: adenoviruses; anthrax; *Bordetella pertussus*; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever, dengue toxoplasmosis; Diphtheria; encephalitis; Enterotoxigenic *E. coli*; Epstein Barr virus; equine encephalitis; equine infectious anemia; equine influenza; equine pneumonia; equine rhinovirus; *Escherichia coli*; feline leukemia; flavivirus; Globulin; haemophilus influenza type b; *Haemophilus influenzae; Haemophilus pertussis; Helicobacter pylori*; Hemophilus; hepatitis; hepatitis A; hepatitis B; Hepatitis C; herpes viruses; HIV; HIV-1 viruses; HIV-2 viruses; HTLV; Influenza; Japanese encephalitis; Klebsiellae species; *Legionella pneumophila*; leishmania; leprosy; lyme disease; malaria immunogen; measles; meningitis; meningococcal; Meningococcal Polysaccharide Group A; Meningococcal Polysaccharide Group C; mumps; Mumps Virus; mycobacteria and; *Mycobacterium tuberculosis*; Neisseria; *Neisseria gonorrhoeae; Neisseria meningitidis*; ovine blue tongue; ovine encephalitis; papilloma; parainfluenza; paramyxovirus; paramyxoviruses; Pertussis; Plague; Pneumococcus; *Pneumocystis carinii*; Pneumonia; Poliovirus; Proteus species; *Pseudomonas aeruginosa*; rabies; respiratory syncytial virus; rotavirus; Rubella; Salmonellae; schistosomiasis; Shigellae; simian immunodeficiency virus; Smallpox; *Staphylococcus aureus*; Staphyiococcus species; *Streptococcus pneumoniae; Streptococcus pyogenes*; Streptococcus species; swine influenza; tetanus; *Treponema pallidum*; Typhoid; Vaccinia; varicella-zoster virus; and *Vibrio cholerae*.

Preferred antigens are those which are known in the art to be useful in as components of vaccines. The antigens may, for example, include various toxoids, viral antigens and/or bacterial antigens. For example, the antigens may include antigens commonly employed in the following vaccines: chickenpox vaccine; diphtheria, tetanus, and pertussis vaccines; haemophilus influenzae type b vaccine (Hib); hepatitis A vaccine; hepatitis B vaccine; influenza vaccine; measles, mumps, and rubella vaccines (MMR); pneumococcal vaccine; polio vaccines; rotavirus vaccine; anthrax vaccines; and tetanus and diphtheria vaccine (Td).

In a preferred aspect, the drug component of the drug-oligomer conjugates is insulin or a functional equivalent thereof, preferably mammalian insulin or a functional equivalent thereof, most preferably human insulin or a functional, equivalent thereof.

An alternative form of insulin suitable for use in the drug-oligomer conjugates of the present invention is insulin lispro, a newly developed analogue of human insulin in which the positions of the amino acids lysine and praline have been switched at the end of the β chain of the insulin molecule (Koivisto, V. A. "The human insulin analogue insulin lispro" Ann Med 1998 June 30:3 260–6). Insulin lispro with lysine at position B28 and proline at position B29 has a weaker tendency for self-association than human insulin. This leads to three major differences in pharmacokinetics: the action begins faster, has a higher peak and the duration is shorter than with human insulin. Thus, insulin lispro has a more precise action profile for the mealtime than human regular insulin. Insulin lispro is recommended to be injected within 15 min before the meal in contrast to 30–40 min for human insulin. Insulin lispro was designed to be used as a mealtime insulin. In another aspect, a patient may be administered (either sequentially or simultaneously), a drug-oligomer conjugate comprising a fast-acting insulin (e.g., lispro) and a drug-oligomer conjugate having a slow acting insulin (e.g., ordinary insulin). In this way, a subject's glucose levels can be (1) quickly brought under control and (2) maintained for an extended period of time, an advantage that is not possible with a quick-acting insulin alone.

4.1.2 Oligomer Component

The drug-oligomers of the present invention comprise an oligomer component. The oligomers of the present invention comprise a hydrophilic component (hydrophile) and a lipophilic component (lipophile).

Suitable lipophilic components include, for example, natural fatty aids or alkyl chains. Preferably, the fatty-acid component is a straight chain molecule having (saturated or unsaturated) carbon atoms and suitably ranges from two (2) to twenty-eight (28) carbon atoms. Most preferably, the fatty acid has from twelve (12) to twenty-two (22) carbon atoms. Unsaturated fatty acids which can be employed as the lipophilic component of the oligomer include, for example, oleic, linoleic and linolenic.

The hydrophilic component is typically a straight or branched PEG polymer and/or a sugar. Where the hydrophilic component is a PEG polymer, the PEG polymer preferably has from 1 to 130 PEG units; more preferably from 1 to 100 PEG units. The hydrophilic component is preferably a small segment of polyethylene glycol (PEG), preferably having 1–10 PEG units, and more preferably 2–8 PEG units. In a highly preferred aspect, the drug is insulin or a functional equivalent of insulin and the PEG polypeptide has 3, 4, 5, 6 or 7 PEG units.

The length and composition of the lipophilic components and the hydrophilic components may be selected to provide a desired degree of lipophilicity, hydrophilicity or amphiphilicity. The carbon chains of the fatty acid or alkyl components may be lengthened to increase lipophilicity, while PEG components may be lengthened to increase hydrophilicity. Where the drug-oligomer conjugate is to be administered orally, the degree of amphiphilicity of the drug-oligomer conjugate should be adjusted to permit the drug-oligomer conjugate to cross the gut epithelium into the bloodstream.

Furthermore, a lipophilic component may be joined to a hydrophilic component by a non-hydrolyzable bond, or by a bond that is not readily hydrolyzable. The hydrophilic component of the lipophile can then be bound by a hydrolyzable bond to the hydrophile component of the oligomer. For example:

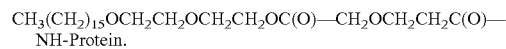

In this way, the hydrophilic aspect of the oligomer can be balanced by increasing the size of the hydrophilic moiety on the lipophilic side of the hydrolyzable bond. Thus, the claimed invention can be alternatively described according to the following general formula:

$$D-[(H-H'_q)L_o]_p \qquad \text{(Formula 10)}$$

wherein D, H and L are as described above; H' is as described for H above; and wherein the H—H bond is hydrolyzable and the H'—L bond is not hydrolyzable; q is a number from 1 to the maximum number of covalent bonding sites on H at which an H' can be attached to H; and L is a number from 1 to the maximum number of covalent bonding sites at which an L substituent can be attached to H'. This arrangement permits the H and H' moieties to be selected so as to balance the hydrophilicity of H against the lipophilicity of L and (accounting for the hydrophilicity or lipophilicity of D) enabling the production of an amphiphilic conjugate, while at the same time, enabling the use of a small H moiety (e.g., H can be a short PEG chain having 2 to 10 PEG units) which enables or retains activity of the hydrolyzed D—H moiety. In other words, the hydrolyzable bond can be positioned at any point along the hydrophilic moiety which provides a hydrolyzed D—H moiety with maximum activity.

Thus, where D is insulin, it is preferable for the H moiety to be a PEG polymer having from 2 to 7 PEG units, more preferably 3, 4, 5 or 6 PEG units, most preferably 3 PEG units; while H' can be any length necessary to balance lipophilicity of the remaining components of the conjugate, resulting in an amphiphilic conjugate that can traverse the intestinal wall (e.g., by interacting with the biological membrane of the cells of the intestine) to enter the bloodstream. In the bloodstream, the H—H' bond will be hydrolyzed, thereby resulting in a insulin-PEG conjugate with improved activity as compared to an unconjugated insulin polypeptide.

A cholesterol or adamantane moiety can be substituted for straight chain fatty acid as the lipophilic component of the oligomers.

Preferred oligomers of the present invention comprise a component selected from the following components:

$$CH_3(CH_2)_n(OC_2H_4)_mOH \qquad \text{(Formula 3)};$$

wherein n=3 to 25 and m=1 to 7;

$$CH_3(CH_2)_n(OC_2H_4)_mOCH_2CO_2H \qquad \text{(Formula 4)};$$

wherein n=3 to 25 and m=1 to 6;

$$CH_3(CH_2)_nCO(OC_2H_4)_mOH \qquad \text{(Formula 5)};$$

wherein n=3 to 25, and m=1 to 7;

$$R-(OC_2H_4)_mCH_2CO_2H \qquad \text{(Formula 6)}$$

wherein m=0 to 5 and R=cholesterol or adamantane; or $$R-OCO(C_2H_4O)_mCH_2CO_2H \qquad \text{(Formula 7)};$$

wherein m=0 to 5;

$$CH_3(CH_2-CH=CH)_6(CH_2)_2CH_2(OC_2H_4)_mOH \qquad \text{(Formula 8)};$$

wherein m=1 to 7;

$$CH_3(CH_2-CH=CH)_6(CH_2)_2CO(OC_2H_4)_mOH \qquad \text{(Formula 9)};$$

wherein m=1 to 7.

Formula 5 is representative oligomers having the H—L configuration in which the H—L bond is hydrolyzable. Formulas 3, 4, 6, 7, 8, and 9, are representative of the H'—L component of oligomers having H—H'—L configuration; the H'—L component as displayed is to be joined to the H component by a hydrolyzable bond, resulting in an H—H'—L oligomer wherein the H—H' bond is hydrolyzable.

Preferred hydrolyzable bonds include, for example, ester (a carboxy group of the lipophile covalently coupled to a hydroxyl group of the hydrophile or a carboxy group of the oligomer covalently coupled to a hydroxyl group of the lipophile) and carbonate. Use of a hydrolyzable bond provides the advantage that when the DHL or DH—H'—L conjugate has crossed the gut epithelium into the hydrophilic environment of the blood stream, the H—L or H—H' component will be excised by hydrolysis of the hydrolyzable bond, thereby releasing the D—H component of the conjugate.

In a preferred mode, where the conjugate is to be administered orally, the length and composition of the lipophilic components and the hydrophilic components may be adjusted to ensure that (1) the conjugate has sufficient amphiphilicity to traverse the gut epithelium, and (2) the H moiety does not eliminate the activity of the therapeutic moiety once the L or H'—L moiety has been severed by hydrolysis of the HA or H—H' hydrolyzable bond. Additionally, the length and composition of the H may be adjusted to optimize the activity of the drug-hydrophile component of the drug-hydrophile conjugate.

The D—H and H'—L bonds are preferably not hydrolyzable. Examples of suitable non-hydrolyzable bonds include, for example, amide (a carboxy group of the hydrophile linked to an amine group of the drug) and carbamate (a chloroformate group of the hydrophile linked to an amine group of the drug). Preferred amine groups of polypeptide drugs for attachment by amide or carbamate bonds are the amine of the N-terminus of the polypeptide or of a nucleophilic amino residue, usually found on the E-amino residue of a lysine residue.

Sugars and other carbohydrates can form convenient spacer groups between the H—L, the H—H' and/or the H'—L groups oligomer, resulting in H—S—L, the H—S—H' and/or the H'—S—L configurations, respectively, where S represents a spacer group. The multiple —OH groups of these compounds form convenient covalent bonding sites for multiple lipophilic components. Preferred carbohydrates are mono and disaccharides. A particularly preferred spacer group is glycerol, as illustrated by the following example:

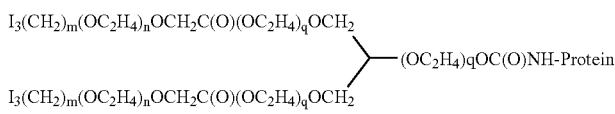

In this example, the hydrolyzable bond is on the opposite side of the glycerin molecule from the protein drug. Thus, upon hydrolysis, the glycerin component remains a part of the drug-hydrophile conjugate, resulting in a DH—S or D H' configuration. However, it will be appreciated that the hydrolyzable bond may be placed on either side of the spacer group, and can thus, when hydrolyzed, also result in conjugates having the OH configuration. Accordingly, the present invention also provides conjugates having the following general formulae:

D—[(H—S$_n$)—L$_o$]$_p$ (Formula 11)

D—[(H—S$_n$—H'$_q$)—L$_o$]p (Formula 12); and

D—[(H—H'$_q$—S$_n$)—L$_o$]p (Formula 13)

wherein D, H, H' and L are as defined above, and S is a spacer group selected from the group consisting of sugars, carbohydrates and glycerol; q is a number from 1 to the maximum number of covalent bonding sites on H; n is a number from 0 to the maximum number of covalent bonding sites on H'; o is a number from 1 to the maximum number of covalent bonding sites on S, when S is present or on H' when S is not present; and p is a number from 1 to the maximum number of covalent bonding sites on D; when S is not present, L is attached to H or H', as in Formulas 1 and 2. Each of the Formulas, 11, 12 and 13 has at least 1 hydrolyzable bond. In Formula 11, the hydrolyzable bond can be S—L or S—H; in Formula 12, the hydrolyzable bond can be S—H or S—H'; in Formula 13, the hydrolyzable bond is H—H'.

4.2 Preparation of Drug-oligdmer Conjugates 4.2.1 Preparation of Polypeptide Component of Drug-oligomer Conjugates Where the drug component of the present invention is a polypeptide, the polypeptide may be prepared according to any method known in the art. In addition to recombinant methods, the polypeptide components may be made by synthetic techniques known in the art, e.g., by use of a polypeptide synthesizer, or other standard chemical methods known in the art (e.g., see Hunkapiller, M., et al., 1984, Nature 310:105–111; Clark—Lewis et al., 1991, *Biochem.* 30:3128–3135 and Merrifield, 1963, *J. Amer. Chem. Soc.* 85:2149–2156. For example, the polypeptides can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). The composition of the polypeptides may be confirmed by amino acid analysis orsequencing (e.g., the Edman degradation procedure; see Creighton, 1983, Proteins, Structures and Molecular Principles, W.H. Freeman and Co., N.Y., pp. 3449) or by protein mapping. The polypeptides of the invention may be synthesized in their entirety by the sequential addition of amino acid residues or alternatively as fragment subcomponents which may be combined using techniques well known in the art, such as fragment condensation (Shin et al., 1992, *Biosci. Biotech. Biochem.* 56:404408; Nyfeler et al., 1992, Peptides, Proc. 12th Amer. Pep. Soc., Smith and Rivier (eds.), Leiden, pp 661–663; and Nokihara et al., 1990, Protein Research Foundation, Yanaihara (ed.), Osaka, pp 315–320). In an alternative embodiment, native polypeptides can be purified from natural sources using standard methods (e.g., immunoaffinity purification).

A newly synthesized polypeptide can be purified using any available method, for example using reverse phase high performance liquid chromatography (RP-HPLC) or other methods of separation based on the size or charge of the polypeptide. Furthermore, the purified polypeptide can be characterized using these and other well known methods such as amino acid analysis and mass spectrometry.

The drug components of the drug-oligomer conjugates of the present invention can be modified in order to facilitate coupling to the oligomer component. Where the drug component is a polypeptide, a functional group may be added to the C-terminus or the N-terminus of the polypeptide or to a side chain of the polypeptide in order to provide a point of attachment for the oligomer. For example, a proline or alanine residue can be added to the N-terminus of a therapeutic polypeptide in order to facilitate attachment of the oligomer component. Suitable modifications are those which do not eliminate the activity of the drug.

Similarly, specific amino acids may be inserted within the amino acid chain of the polypeptide or may replace an amino acid of the therapeutic in order to facilitate attachment of the oligomer, provided that such modification does not eliminate the activity of the polypeptide.

Thus, for example, one or more amino acids within a polypeptide drug can be modified or substituted, as for example, by a conservative amino acid substitution of one or more amino acids. A conservative amino acid substitution change can include, for example, the substitution of one acidic amino acid for another acidic amino acid, of one hydrophobic amino acid for another hydrophobic amino acid or other conservative substitutions known in the art, including the use of non-naturally occurring amino acids, such as Nle for Leu or ornithine (Orn) or homoArginine (homoArg) for Arg.

In addition to the above types of modifications or substitutions, a mimic of one or more amino acids, otherwise known as a polypeptide mimetic or peptidominetic, can also be used. As used herein, the term "mimic" means an amino acid or an amino acid analog that has the same or similar functional characteristic of an amino acid. Thus, for example, a (D)arginine analog can be a mimic of (D)arginine if the analog contains a side chain having a positive charge at physiological pH, as is characteristic of the guinidinium side chain reactive group of arginine. A polypeptide mimetic or peptidomimetic is an organic molecule that retains similar polypeptide chain pharmacophore groups as are present in the corresponding polypeptide.

The substitution of amino acids by non-naturally occurring amino acids and peptidomimetics as described above can enhance the overall activity or properties of an individual polypeptide based on the modifications to the side chain functionalities. For example, these types of alterations can be employed along with the oligomer components of the present invention to further enhance the polypeptide's resistance to enzymatic breakdown and/or to improve biological activity.

4.2.2 Synthesis of Drug-oligomer Conjugates

A general synthesis scheme for preparing the drug-oligomer conjugates of the present invention is provided in FIG. 1.

In the synthesis of oligomers containing fatty acids and polyethylene glycols, where the ethylene glycol is connected to the fatty acid in a hydrolyzable ester bond, it is desirable to start with the acid chloride of the fatty acid or its acid anhydride. A desired polyethylene glycol having two free hydroxyls at the termini is then treated in inert solvent with equal molar equivalent of acid chloride or acid anhydride. The glycol unit is first dissolved in inert solvent and treated with organic base before the addition of the acid chloride or acid anhydride. The product is extracted from the reaction medium and further purified using column chromatography:

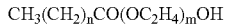

wherein n = 0 to 24, and m = 2 to 130.

In some instances, it is desirable to prepare oligomers that have stronger hydrolyzable bond, such as amide. The acid chloride or the acid anhydride of the selected fatty acid is treated with amino derivative of polyethylene glycol in a controlled reaction condition to affect only the amino residue and not the hydroxyl portion. Selectivity can also be ensured by converting the fatty acid into N-hydroxysuccinimide ester and reacting with the amino residue of the polyethylene glycol.

$$CH_3(CH_2)_nCOCl + NH_2CH_2CH_2(OC_2H_4)_mOH$$
 Pyridine
$$CH_3(CH_2)_nCONHCH_2CH_2(OC_2H_4)_mOH$$

wherein n = 0 to 24, and m = 2 to 130;

$$CH_3(CH_2)_nCOONSU + NH_2CH_2CH_2(OC_2H_4)_mOH$$
 THF/TEA
$$CH_3(CH_2)_nCONHCH_2CH_2(OC_2H_4)_mOH$$

wherein n = 0 to 24, and m = 2 to 130.

The oligomer can be coupled to the peptide drug by converting the free hydroxyl moiety of the oligomer to N-hydroxysuccinimide ester (NSU). The N-hydroxysuccinimide group reacts readily with the nucleophilic amino residue of the peptide.

$$CH_3(CH_2)_mCONHCH_2CH_2(OC_2H_4)_nOCONSU + Peptide$$
$$CH_3(CH_2)_mCONHCH_2CH_2(OC_2H_4)_nOCO\text{-Peptide}$$

wherein n = 0 to 24, and m = 2 to 130.

In the synthesis of oligomers in which the lipophilic portion of the oligomers is connected to the hydrophilic portion by ether linkage, the desired polyethylene glycol (hydrophile) is first protected. One of the two free hydroxyls at the termini is protected with a trityl group in pyridine using one mole of trityl chloride. The protected polyethylene glycol is dissolved in a suitable inert solvent and treated with sodium hydride. Bromo or tosylate derivative of the lipophilic portion is dissolved in inert solvent and added to the solution of the protected polyethylene glycol. The product is treated with a solution of para-toluenesulfonic acid in anhydrous inert solvent at room temperature. The desired product is extracted in inert solvent and purified by column chromatography. The structures of the transformation are depicted below:

$$CH_3(CH_2)_nBr + HO(C_2H_4O)_mTrityl$$
 NaH / THF
$$CH_3(CH_2)_n(OC_2H_4)O_mTrityl$$
 P-TSA
$$CH_3(CH_2)_n(OC_2H_4)_mOH$$

wherein n = 0 to 24, and m = 2 to 130.

The lipophilic portion is preferably selected from the group consisting of alkyl, cholesterol and adamantyl moieties.

In the synthesis of oligomers where the lipophilic portion of the oligomer is connected to the hydrophilic portion by an ether bond and the terminal ends in a carboxylic acid moiety, it is desirable to protect the carboxylic group. Polyethylene glycol having free hydroxyl group at one end and carboxylic group at the other end is selected. The carboxylic group is protected by esterification. The protected polyethylene glycol is dissolved in a suitable inert solvent (e.g., THF) and treated with sodium hydride. Bromo or tosylate derivatives of the lipophilic portion are dissolved in inert solvent and added to the solution of the protected polyethylene to glycol. The product is treated with solution of sodium hydroxide to liberate free acid. The desired product is extracted in inert solvent and purified by column chromatography. The structures of the transformation are depicted below:

$$CH_3(CH_2)_nBr + HO(C_2H_4O)_mCH_2CO_2C_2H_5$$
 NaH / THF
$$CH_3(CH_2)_n(OC_2H_4)_mOCH_2CO_2C_2H_5$$
 NaOH
$$CH_3(CH_2)_n(OC_2H_4)_mOCH_2CO_2H$$

wherein n = 0 to 24, and m = 2 to 130.

The lipophilic portion is preferably selected from the group consisting of alkyl, cholesterol and adamantyl moieties.

This group of acidic oligomers can be coupled to peptide drugs by first reacting the carboxylic group with N-hydroxysuccinimide (NSU) to form an easily leavable group. A solution of the activated oligomers in inert solvent is then treated with the desired peptide drug dissolved in a suitable solvent. Inverse addition may be selected.

$$CH_3(CH_2)_n(OC_2H_4)_mOCH_2COH_2 + NSU$$
 DCC
$$CH_3(CH_2)_n(OC_2H_4)_mOCHCO_2NSU$$
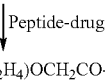 Peptide-drug
$$CH_3(CH_2)_n(OC_2H_4)OCH_2CO\text{-Peptide}$$

Sometimes it is desirable to replace the lipophilic moiety with lipophilic sugars. The sugar moiety is first esterified with desired fatty acid chloride to obtain selective or partial acylation. The product is treated in inert solvent with diacid chloride of desired dicarboxylic acid derivative of polyethylene glycol.

Reaction is conducted with one molar equivalent of each reacting moiety. This reaction leaves one end of the hydrophile bearing acid chloride, which is further converted to N-hydroxysuccinimide ester. The activated ester is reacted with peptide drug in suitable inert solvent.

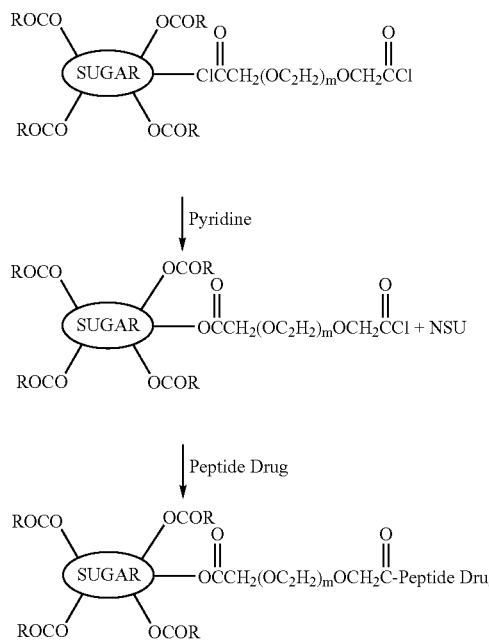

Where R is selected from the group consisting of fatty acid, alkyd$_{1-26}$, cholesterol and adamantane, and where m is a number from 1 to 130.

4.3 Therapeutic Methods

The invention provides methods of treatment and prevention by administration to a subject of an effective amount of an drug-oligomer conjugates of the invention.

One embodiment of the invention provides for methods of administering a pharmaceutical composition comprising a therapeutically effective amount of a drug-oligomer conjugates according to the present invention.

Methods of introduction include but are not limited to oral, parenteral, rectal, topical, sublingual, mucosal, nasal, opthalmic, subcutaneous, intramuscular, intravenous, transdermal, spinal, intrathecal, intra-articular, intra-arterial, sub-arachnoid, bronchial, lymphatic, and intrauterine administration. The conjugates may be administered by any convenient route, for example by infusion or bolus injection, by absorption through epithelial or mucocutaneous linings (e.g., oral mucosa, rectal and intestinal mucosa, etc.) and may be administered together with other biologically active agents. Preferred routes are oral and parenteral; most preferred is oral. Administration can be systemic or local.

In certain circumstances, it may be desirable to introduce the pharmaceutical compositions of the invention directly into the central nervous system by any suitable route, including intraventricular and intrathecal injection; intraventricular injection may be facilitated by an intraventricular catheter, for example, attached to a reservoir, such as an Ommaya reservoir.

Pulmonary or nasal administration can also be employed, e.g., by use of an inhaler or nebulizer, and formulation with an aerosolizing agent.

In another embodiment, the conjugates can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Other controlled release systems are discussed in the review by Langer (Science 249:1527–1533 (1990)).

The subject is preferably an animal, including, but not limited to, animals such as cows, pigs, horses, chickens, cats, dogs, etc., and is preferably a mammal, and most preferably human.

4.4 Pharmaceutical Compositions

The present invention contemplates the use of pharmaceutical compositions for veterinary and medical use. The pharmaceutical compositions generally comprise one or more drug-oligomer conjugates of the present invention as therapeutic ingredients. Such pharmaceutical compositions may include pharmaceutically effective carriers, and optionally, may include other therapeutic ingredients. The carrier or carriers must be pharmaceutically acceptable in the sense that they are compatible with the therapeutic ingredient(s) and are not unduly deleterious to the recipient thereof. Compatible carriers are those which do not eliminate the activity of the therapeutic ingredient(s). Preferred carriers are those which do not significantly diminish the activity of the therapeutic ingredient(s). The therapeutic ingredient(s) are provided in a therapeutically effective amount.

In a preferred aspect, the therapeutic ingredient(s) of the pharmaceutical compositions include an insulin-PEG$_{1-10}$-lipophile conjugate.

The pharmaceutical compositions of the present invention will contain a therapeutically effective amount of the drug-oligomer conjugates, preferably in purified form, together with a suitable amount of carrier so as to provide the form for proper administration to the patent. The formulation should suit the mode of administration.

Various delivery systems are known and can be used to administer a conjugate of the invention, e.g., encapsulation microcapsules. Preferred pharmaceutical formulations according to the present invention include emulsions and microemulsions. Most preferred are microemulsions.

The term "carrier" refers to a diluent, adjuvant, excipient, or other vehicle with which the conjugate is administered. Such pharmaceutical carriers can be sterile liquids, such as water and oils, including those of petroleum, animal, vegetable or synthetic origin, such as peanut oil, soybean oil, mineral oil, sesame oil and the like. Other examples of suitable pharmaceutical carriers are described in "Remington's Pharmaceutical Sciences" by E. W. Martin. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

In a preferred embodiment, the composition is formulated in accordance with routine procedures as a pharmaceutical composition adapted for intravenous administration to human beings. Water is a preferred carrier when the pharmaceutical composition is administered intravenously. Saline solutions and aqueous dextrose and glycerol solutions can also be employed as liquid carriers, particularly for injectable solutions. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Oral formulations can include standard carriers such as pharmaceutical grades of mannitol, lactose, starch, magnesium stearate, sodium saccharine, cellulose, magnesium carbonate, etc.

The composition, if desired, can also contain wetting or emulsifying agents, or pH buffering agents.

The compositions can take the form of solutions, suspensions, syrups, emulsions, microemulsions, elixirs, tablets, pills, capsules, lozenges, powders, sustained-release formulations and the like. The composition can also be formulated as suppositories, with traditional binders and carriers such as triglycerides. Suppositories generally contain active ingredient in the range of 0.5% to 10% by weight; oral formulations preferably contain 10% to 95% active ingredient.

In a preferred aspect, the pharmaceutical compositions of the present invention are formulated as emulsions or microemulsions; microemulsions are especially preferred.

Emulsions are colloidal dispersions comprising to immiscible liquids (e.g., oil and water), one of which is disperse as droplets within the other (Block, L. et al. "Pharmaceutical Emulsions and Microemulsions," Pharmaceutical Dosage Forms: Disperse Systems, Vol. 2, pp. 47–109 (1996)). Emulsions are generally prepared by subjecting the emulsion components to milling or comminution processes. Emulsions include systems that are extensions of two-phase emulsions in which a discontinuous, or internal, phases themselves comprise emulsified systems. Each internal phase, in turn, may be polydisperse, resulting in tertiary, quaternary or higher order emulsions. Emulsions useful of the present intention therefore include, for example, W/O, O/W, W/O/W, O/W/O, and the like. The emulsion compositions of the invention may also comprise a third nonliquid phase, e.g., a phase including solid particles or lyotropic liquid crystals.

A microemulsion is generally defined as a system of water, oil and amphiphile which is a single optically isotropic and thermodynamically stable liquid. Microemulsions are generally prepared by first dispersing and oil in an aqueous surfactant solution and then adding a sufficient amount of an intermediate chain alcohol to form a transparent system.

A wide variety of polar and nonpolar chemical components are available for use as the immiscible phase of an emulsion. Polar components include, for example, polyols (e.g., butylene glycol, glycerin, polyethylene glycols, propylene glycol) and water. Nonpolar components include, for example esters (e.g., fats, lanolin, isopropyl myristate, isopropyl palmitate, glyceryl monostearate and vegetable oils), ethers (e.g., perfluoropolyethers and polyoxypropylenes), fatty acids, fatty alcohols, hydrocarbons (e.g. butane, propane, microcrystalline waxes, mineral oils, petrolatum and squalene), halohydrocarbons (e.g., perfluorocarbons and chlorofluorocarbons), plant and animal waxes, and silicone fluids.

The emulsion may also comprise various emulsion stabilizers, preservatives, antioxidants, and other functional ingredients.

Surfactants are useful in the emulsions and microemulsions of the present invention to decrease the energy required to disrupt phase continuity and achieve complete phase dispersal by lowering enter facial tension. Suitable surfactants for use in the emulsion compositions of the present invention may comprise anionic, cationic, Zwitterionic, amphoteric, and nonionic surfactants. Preferred surfactants are those having an hydrophilic-lipophilic balance (HLB) in the range of 6–20; more preferred are those having an HLB in the range of 8–20; still more preferred are those having an HLB in the range of 10–20 and most preferred are those having an HLB in the range of from 13 to 20. Alternatively, the preferred surfactants are those which result in a stable, translucent to clear solution; most preferred are those which result in a clear solution.

Suitable emulsion stabilizers include, for example: lyophilic colloids, polysaccharides, acacia, agar, alginic acid, carrageenan, guar gum, karaya gum, tragacanth, xantham gum, clays, microcrystalline cellulose, oxides and hydroxides, pyrogenic or fumed silica, gelatin, carbomer resins, cellulose ethers, and the like.

Preservatives (e.g., anti-microbial agents) and antioxidants (e.g., citric acid, EDTA, phenylalanine, phosphoric acid, tartaric acid, tryptophane, ascorbic acid, sodium bisufate and sodium sulfite) may also be employed in the emulsions and microemulsions of the present invention.

The mode of administration and dosage forms will of course affect the therapeutic amounts of the compounds which are desirable and efficacious for the given treatment application. It will be readily apparent to one of skill in the art that a therapeutically effective amount will vary based on factors such as the weight and health of the recipient, the mode of administration and the type of medical disorder being treated.

For example, suitable doses of an insulin conjugate may generally be in the range of from 0.1 mg/kg to 5 mg/kg, preferably 0.1 mg/kg to 2 mg/kg, more preferably 0.2 mg/kg to 0.3 mg/kg. Effective doses may be extrapolated from dose-response curves derived from in vitro or animal model test systems.

Accessory ingredients may, without limitation, include diluents, buffers, flavoring agents, disintegrants, surfactants, thickeners, lubricants, preservatives, and/or antioxidants.

The drug-oligomer conjugates of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with one or more of the ingredients of the pharmaceutical compositions of the invention. A notice in the form prescribed by a governmental agency regulating the manufacture, use or sale of pharmaceuticals or biological products, can be optionally associated with such container(s). Such notices can reflect approval by the agency for manufacture, use or sale for human administration.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Throughout this specification reference has been made to various patent and non-patent references. The entire disclosure of each of these references is incorporated herein by reference, as is the entire disclosure of each of the following references: U.S. Pat. No. 5,681,811 entitled "Conjugation—Stabilized Therapeutic Agent," issued Oct. 28, 1997; U.S. Pat. No. 5,438,040, entitled "Conjugation—Stabilized Polypeptide Compositions, Therapeutic Delivery and Diagnostic Formulations Comprising Same, and Method of Making and Using the Same," issued Aug. 1, 1995; U.S. Pat. No. 5,359,030 entitled "Conjugation—Stabilized Polypeptide Compositions, Therapeutic Delivery and Diagnostic Formulations Comprising Same, and Method of Making and Using the Same," issued Oct. 25, 1994; U.S. Pat. No. 6,191,105, entitled "Hydrophilic and Lipophilic Balanced Microemulsion Formulations of Free-Form and/or Conjugation—Stabilized Therapeutic Agents such as Insulin," issued Feb. 20, 2001; U.S. patent application Ser. No. 09/134,803, entitled "Blood-Brain Barrier Therapeutics.", filed Aug. 14, 1998; Chien, et al. *Drug Dev. Ind. Pharm.* 15:1601–1634 (1989); Radhakrishnan; et al. *Proc. Intl. Symp. Control Rel. Bioactive Mater.* 25:124–125 (1998); and Ekwuribe, N. AAPS Ann. Meeting Abst. S-102—S-103 (1998).

5. EXAMPLES

Conjugates of the present invention were evaluated in a mouse blood glucose assay to examine their potency. Conjugates formulated in microemulsion were further evaluated for oral activity in pancretectotized diabetic dogs.

5.1 Synthesis and Characterization of Hydrolyzable and Nonhydrolyzable Oligomer Insulins Hydrolyzable oligomers were synthesized by coupling fatty acid chlorides with an equivalent mole of polyethylene glycol. Nonhydrolyzable oligomers were synthesized by coupling alkyl bromide with monosodium salt of appropriate polyethylene glycol. The oligomers were activated with N-hydroxysuccinimide and coupled to insulin, purified, and characterized by MALDI(TOF)-MS to determine number of oligomers on a mole of insulin. The basic synthetic scheme is illustrated in FIG. 1.

5.2 Triethylene Glycol and $PEG_9$

Triethylene Glycol (100g, 0.67moles) was weighed in an Erlenmeyer flask, dissolved in Methylene chloride and treated with $MgSO_4$. The $MgSO_4$ was filter using a sintered glass funnel with celite. Methylene chloride was removed and the composition was dried overnight over $P_2O_5$ on high vacuum.

In a clean, dry, two neck, round bottom flask equipped with a stir bar, calcium sulfate tube and addition funnel, dried Triethylene Glycol (49.72g, 0.33 moles) was weighed in the flask and anhydrous THF (200 ml) was added. One mole equivalent of Triethylamine (15.8 ml, 0.11 moles) was added to the vessel. The reaction flask was cooled to 5° C. From an addition funnel Oleoyl chloride (33.10g, 0.11 moles) was added dropwise over 10 minutes in twice the volume of THF. After addition, the reaction was stirred for 3 h, a precipitate was formed.

TLC: silica gel Eluent: 3:2 Ethyl Acetate:Hexane

THF was removed from filter precipitate by rotatory evaporation. Methylene chloride was added to the residue and washed with deionized water (2×50 ml), brine (2×75 ml) and deionized water(3×50 ml).

The product was purified using a Silica Gel Column 4.6×39.0 cm, and Eluent: 3:2 Ethyl Acetate:Hexane.

In a two neck flask the Oleate $PEG_3$ (2.0g, 4.8 mmoles) was weighed. Methylene Chloride was added and stirred to dissolve the polymer. Triethylamine (0.7 ml, 4.9 mmoles) was added and the reaction mixture was cooled. The reaction vessel was thoroughly cooled and 4-nitrophenyl chloroformate (1.0g, 4.9 mmoles)) dissolved in methylene chloride was slowly added, resulting in an exothermic reaction. The reaction was stirred at room temperature for 6 h. After 6 h the methylene chloride was removed by rotatory evaporation. Ether was added to the flask and precipitate was formed. The solution was filtered to remove the precipitate. The filtrate was dried over $MgSO_4$, then the ether was filtered and removed, yielding an orange-yellow oil.

A C18 Reverse Phase Column was prepared in the laboratory and equipped with a perstaltic pump. 2.5×26.5 cm. Eluent: 30% Deionized water in Isopropanol Insulin (1.503 g, 0.26 mmoles) was weighed in a round bottom flask equipped with a stir bar. While stirring, DMSO (5 ml) was carefully added and allowed to stir until dissolved. Triethylamine (2.08 mmoles) was added and stirred for 10 minutes. Activated oleate triethylene glycol in minimum amount of DMSO (2 ml) was added carefully all at once and stirred for 3 h at room temperature. The reaction was monitored via HPLC every 30 mins. The conjugate was purified using a preparative HPLC.

5.2.1 Laurate and Oleate $PEG_n$

The polymers (commercially available) were dissolved in methylene chloride and washed with saturated NaCl (3×50 ml), Sodium bicarbonate (3×50 ml) and deionized water (3×50 ml) to remove any free PEG's. The solution was dried as described above for triethylene glycol.

In a two neck flask, the Laurate PEGs (21.72 g, 54.3 mmoles) was weighed. Methylene Chloride was added and stirred to dissolve the polymer. Next, triethylamine (7.56 ml, 54.3 mmoles) was added, the reaction mixture was cooled and 4-nitrophenyl chloroformate (10.72 g, 53.0 mmoles). Once addition was complete, the reaction was stirred at room temperature for 6 h. After 6 h the methylene chloride was removed by rotatory evaporation. Ether was added to the flask; a precipitate was formed and was filtered. The filtrate was dried over $MgSO_4$ and filtered to remove the solvent. An orange-yellow oil was obtained.

A C18 Reverse Phase Column was prepared and equipped with a perstaitic pump. 2.5×26.5 cm, using 30% deionized water in Isopropanol as the eluent.

Insulin (1.52 g, 0.262 mmoles) was weighed in a round bottom flask with a stir bar. DMSO (5 ml) was carefully added while stirring. Triethylamine (2.1 mmoles) was added and stirred for 10 minutes. Activated laurate $PEG_5$ (0.152 g, 0.262 mmoles) was dissolved in a minimum amount of DMSO (2 ml). This was carefully added all at once and stirred for 3 h at room temperature. The reaction was monitored via HPLC every 30 mins. The conjugate was purified using a preparative HPLC Vydac C18 HPLC 22 idmm×250 mml.

5.3 Preparation of formulation used for Hydrolyzable TEG insulin

First a blank microemulsion was prepared having the following composition:

TABLE 1

Composition of Microemulsion

| Ingredient | Quantity, gm/100 mL |
|---|---|
| Vitamin E TPGS | 2.01 g |
| Labrasol | 38.24 |
| Gelatin Type B, 2% solution | 0.6 g |
| Safflower oil | 0.81 g |
| Capmul MCM | 0.80 g |
| Soy lecithin | 1.10 g |
| Methyl Paraben | 0.004 g |
| Propyl Paraben | 0.020 g |
| L-Ascorbic acid palmitate | 0.010 g |
| Peppermint oil | 0.004 g |
| Water for injection | 54.769 g + 1.19 g |
| Sodium phosphate mono basic anhydrous | 0.03 g |
| Sodium phosphate dibasic anhydrous | 0.14 g |
| Nitrogen | Used during processing and is present in the headspace of the product vial |

5.3.1 Preparation of the Blank Microemulsion

The blank microemulsion was prepared on a weight by weight basis using a five-step procedure.

Step 1. Preparation of oil mixture: A mixture of soybean oil, Caprnul MCM, safflower oil, methyl paraben NF, propyl paraben NF, and L-ascorbic acid palmitate NF was sonicated at 50° C. under nitrogen for 10 minutes to obtain a clear yellow solution.

Step 2. Preparation of emulsifier mixture: A glass container containing a mixture of Labrasol and Vitamin-E-TPGS was sonicated at 50° C. for 10 minutes to obtain a clear solution.

Step 3. Preparation of 100 mM sodium phosphate buffer, pH 7.4: Sodium phosphate monobasic anhydrous and sodium dibasic phosphate anhydrous were dissolved in de-ionized water+and the solution was filtered through a 0.2 μm filter. The final pH of the solution was approximately 7.4.

Step 4. Preparation of final formulation: Hexyl insulin M2 was dissolved in a sterile 150 ml vial containing sodium phosphate buffer, sterile water, gelatin solution and emulsifier mixture. The oil mixture was added dropwise from step 1 to the above mixture. Nitrogen was sparged over headspace and the vial was sealed with a Teflon-coated flat bottom stopper. The solution was sonicated at room temperature for 2 minutes. The final composition was a clear solution.

Step 5. Filling and sealing of the drug product solution: Ten ml of the bulk drug product solution was aliquoted in 10-ml vials and sealed with a Teflon coated flat bottom stopper. The headspace was sparged with nitrogen NF.

5.3.2 Preparation of Insulin TEG Oligomers

All compounds used in this series have limited water solubility.

Preparation of formulated Insulin TEG oleate mixture: 58.6 mg (85% pure) of TEG oleate mixture was dissolved in 5 ml of ME 365 Blank microemulsion.

Preparation of Insulin PEG$_3$ Oleate mono conjugates (M1+M2) mixture in microemulsion: 65.8 mg (85% pure) was dissolved in 12.5 9 (12 ml) of the formulation 4.23 mg/ml.

Preparation of Insulin TEG Octanoate mixture in microemulsion: 57.3 mg (85% pure) was dissolved in 5 ml of the formulation.

Preparation of Insulin TEG palmitate mixture in microemulsion: 58.9 mg (85% pure) was dissolved in 5 ml of the formulation.

Preparation of Insulin PEG 9 Oleate mono conjugates (M1+M2) mixture in microemulsion: 2 mg (85% pure) was dissolved in 0.2 ml of the formulation 9.17 mg/ml.

Preparation of Insulin PEGg Oleate diconjugate in microemulsion: 2 mg (85% pure) was dissolved in 0.2 ml of the formulation 5.78 mg/ml.

Preparation of Insulin TEG DHA conjugate mixture: 70 mg of mono and diconjugate mixture was dissolved in 50 ml of blank emulsion.

5.4 Potency Evaluation

Six paired dose groups of 5 male CF-1 mice (~25 g unfasted) received subcutaneous injections of either bovine insulin or modified insulin. Pre- and post-experimental baselines were established with two vehicle groups. An additional 25 μg/kg insulin dose group served as the internal control. Mice were terminally bled 30 minutes post-dose and blood glucose was measured with a glucometer (ONE TOUCH®). The biological potency of the modified insulin was then calculated relative to a bovine insulin standard curve. Calculations were based upon the assumption that bovine insulin has a potency of 27.5 IU/mg.

TABLE 2

Mouse Blood Glucose Assay

| Insulin Conjugate | Number of Oligomers | Potency IU/mg |
|---|---|---|
| Bovine insulin | none | 27.5 |
| Insulin PEG$_9$ Hexanoate | Mono | 21.3 |
| Insulin PEG$_9$ Stearate | Mono | 15.3 |
| Insulin PEG$_9$ Stearate (Buffer Storage) | ND | 25.8 |
| Insulin PEG$_{10}$ Stearyl Ether | ND | 0.0 |
| Insulin PEG$_9$ Oleate | Mono | 19.0 |
| Insulin PEG$_{10}$ Oleyl Ether | Mono | 0.0 |
| Insulin PEG$_3$ Methyl Ether | Mono | 43.6 |

5.5 Evaluation in Diabetic Dog

Two dogs were used for each compound. Compounds are formulated in water in oil microemulsion and evaluated at a dose of 1–2 mg/kg. Twenty milliliters of the formulation was administered orally to each dog and the formulations were chased with 20 ml of water. Plasma glucose and insulin levels were monitored at different time intervals.

TABLE 3

Oral activity of New Insulin Derivatives in Pancreatectomized Dogs

| Conjugate Studied[a] | No. animals | Dose Mg/kg | Dmax % | Cmax µU/ml |
|---|---|---|---|---|
| PEG$_3$-insulin | N = 2 | 2 | 62 | 181 |
| Galactosamine-PEG$_{14}$-insulin conjugate[a][b] | N = 2 | 2 | 52 | 35 |
| PEG$_3$-octanoate-insulin conjugate | N = 2 | 1 | 27 | 43 |
| PEG$_3$-oleate-insulin conjugate | N = 2 | 1 | 49 | 27 |

[a] All conjugates studied were mixtures of mono, di and tri-conjugated insuliun.

[b] The basic structure of the galactosamine-PEG$_{14}$-insulin conjugate is as follows:

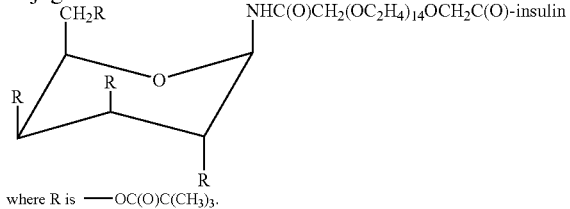

5.6 Results and Discussion

Potency Evaluation: Comparison of activities of hydrolyzable and nonhydrolyzable conjugates shows that the conjugates with hydrolyzable ester bonds produce good in vivo biological activity (Table 2). The activity arises from insulin conjugate that has lost the fatty acid moiety through chemical or biological hydrolysis. Long storage of sample in buffer produces increased activity. HPLC analysis reveals that the fatty acid moiety is hydrolyzed. Nonhydrolyzable conjugates, with long-chain fatty acid and short-chain PEG produce negligible activity.

Evaluation in Pancreatectomized Dogs: The potency assay shows that methyl triethylene glycol conjugate produces the best result (Table 2). On this basis, we have chosen short chains of polyethylene glycol for fatty acid esterification to form oligomer components. Results of four different conjugates formulated in microemulsion are presented. Methyl triethylene glycol conjugates produce good glucose reduction. (Table 3). Two other conjugates bearing high proportion of hydrolyzable fatty acid components produce prolonged glucose reduction (FIGS. 2, 3).

Conclusions: Synthesis of chemically modified insulin with hydrolyzable amphiphillic oligomers has been accomplished. Products formulated in microemulsion have been evaluated orally in diabetic (i.e., pancreatectomized) dogs. Prolonged glucose reduction following oral administration of the insulin-oligomer products has been achieved.

We claim:

1. A drug-oligomer conjugate having the following general formula:

$$D-[(H-H'_q)-L_o]_p \quad \text{(Formula 10)}$$

wherein

D is insulin or a functional equivalent thereof;

H is a PEG polymer having from 1 to 10 PEG units;

H' is a hydrophilic moiety;

L is a lipophilic moiety;

the H—H' bond is hydrolyzable;

q is a number from 1 to the maximum number of covalent bonding sites at which H' can form a bond with H;

o is a number from 1 to the maximum number of covalent bonding sites at which L can form a bond with H'; and p is a number from 1 to the maximum number of covalent bonding sites at which $-[(H-H'_q)-L_o]$ can form a bond with D.

2. The drug-oligomer conjugate of claim 1, wherein H, H' and L are selected and arranged such that the drug-oligomer conjugate is amphiphilic.

3. The drug-oligomer conjugate of claim 1, wherein H is a PEG polymer having from 2 to 8 PEG units.

4. The drug-oligomer conjugate of claim 1, wherein H is a PEG polymer having from 2 to 7 PEG units.

5. The drug-oligomer conjugate of claim 1, wherein H is a PEG polymer having 3 PEG units.

6. The drug-oligomer conjugate of claim 1, wherein H is a PEG polymer having 4 PEG units.

7. The drug-oligomer conjugate of claim 1, wherein H is a PEG polymer having 5 PEG units.

8. The drug-oligomer conjugate of claim 1, wherein H is a PEG polymer having 6 PEG units.

9. The drug-oligomer conjugate of claim 1, wherein H' is a hydrophilic moiety selected from the group consisting of straight or branched PEG polymers and sugars.

10. The drug-oligomer conjugate of claim 1, wherein H' is a straight PEG polymer.

11. The drug-oligomer conjugate of claim 10, wherein the PEG polymer has from 1 to 130 PEG units.

12. The drug-oligomer conjugate of claim 10, wherein the PEG polymer has from 1 to 100 PEG units.

13. The drug-oligomer conjugate of claim 1, wherein L is a lipophilic moiety selected from the group consisting of alkyl moieties, cholesterol, and fatty acid moieties.

14. The drug-oligomer conjugate of claim 1, wherein L is an alkyl moiety.

15. The drug-oligomer conjugate of claim 1, wherein L is cholesterol.

16. The drug-oligomer conjugate of claim 1, wherein L is a fatty acid moiety.

17. The drug-oligomer conjugate of claim 16, wherein the fatty acid moiety has between 2 and 28 carbon atoms.

18. The drug-oligomer conjugate of claim 16, wherein the fatty acid moiety has between 12 and 22 carbon atoms.

19. The drug-oligomer conjugate of claim 1, wherein D is insulin or insulin lispro.

20. The drug-oligomer conjugate of claim 1, wherein the H'—L bond is non-hydrolyzable.

21. The drug-oligomer conjugate of claim 1, wherein H' and L are present as a component H'—L having the formula $CH_3(CH_2)_n(OC_2H_4)_mOH$ (Formula 3), wherein n=3 to 25 and m=1 to 7.

22. The drug-oligomer conjugate of claim 1, wherein H' and L are present as a component H'—L having the formula $CH_3(CH_2)_n(OC_2H_4)_mOCH_2CO_2H$ (Formula 4), wherein n=3 to 25 and m=1 to 6.

23. The drug-oligomer conjugate of claim 1, wherein H' and L are present as a component H'—L having the formula $R-(OC_2H_4)_mCH_2CO_2H$ (Formula 6), wherein m=0 to 5 and R=cholesterol or adamantane.

24. The drug-oligomer conjugate of claim 1, wherein H' and L are present as a component H'—L having the formula $CH_3(CH_2-CH=CH)_6(CH_2)_2CH_2(OC_2H_4)_mOH$ (Formula 8), wherein m=1 to 7.

25. The drug-oligomer conjugate of claim 1, wherein H' and L are present as a component H'—L having the formula $CH_3(CH_2-CH=CH)_6(CH_2)_2CX(OC_2H_4)_mOH$ (Formula 9), wherein m=1 to 7.

* * * * *